United States Patent [19]
Bundgaard et al.

[11] Patent Number: 5,073,641
[45] Date of Patent: Dec. 17, 1991

[54] PRODRUG DERIVATIVES OF CARBOXYLIC ACID DRUGS

[76] Inventors: Hans Bundgaard, Tjørnevej 36, DK-2970 Horsholm; Niels M. Nielsen, Cumberlandsgade 15, st.th., DK-2300 Copenhagen, both of Denmark

[21] Appl. No.: 188,407

[22] PCT Filed: Aug. 25, 1987

[86] PCT No.: PCT/DK87/00104
§ 371 Date: Apr. 26, 1988
§ 102(e) Date: Apr. 26, 1988

[87] PCT Pub. No.: WO88/01615
PCT Pub. Date: Mar. 10, 1988

[30] Foreign Application Priority Data

Aug. 26, 1986 [DK] Denmark ............... 4066/86

[51] Int. Cl.$^5$ .............................................. C07C 69/76
[52] U.S. Cl. ........................................ 560/56; 548/500; 549/494; 560/39; 560/49; 560/153; 560/105
[58] Field of Search ............... 560/56, 39, 49, 105, 560/153; 548/500; 549/494

[56] References Cited
FOREIGN PATENT DOCUMENTS 0106541 4/1984 European Pat. Off. .
0224178 6/1987 European Pat. Off. .
0227355 7/1987 European Pat. Off. .
0237051 9/1987 European Pat. Off. .
86/00066 1/1986 World Int. Prop. O. .

OTHER PUBLICATIONS
CA vol. 106 #78187t, Mar. 16, 1987.
Ehrhart, G. et al., Arzneimittel 1972, 2, 432.

Primary Examiner—Paul J. Killos
Attorney, Agent, or Firm—Birch, Stewart, Kolasch & Birch

[57] ABSTRACT

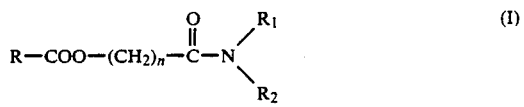

Novel ester derivatives of carboxylic acid medicaments of formula (I), wherein R—COO—represents the acyloxy residue of a carboxylic acid drug or medicament, n is an integrer from 1 to 3, and $R_1$ and $R_2$ are the same or different and are selected from a group consisting of an alkyl, an alkenyl, an aryl, an aralkyl, a cycloalkyl and which group may be unsubstituted or substituted, or $R_1$ and $R_2$ together with the N forms a 4-, 5-, 6- or 7-membered heterocyclic ring, which in addition to the nitrogen atom may contain one or two further heteroatoms selected from the group consisting of nitrogen, oxygen and sulfur and which heterocyclic group may be substituted. These compounds are highly biolabile prodrug forms of the corresponding carboxylic acid compounds and are highly susceptible to undergoing enzymatic hydrolysis in vivo whereas they are highly stable in aqueous solution. The novel derivatives are less irritating to mucosa than the parent carboxylic acids and may provide an improved bio-availability of the drugs.

8 Claims, 3 Drawing Sheets

PRODRUG DERIVATIVES OF CARBOXYLIC ACID DRUGS

BACKGROUND OF THE INVENTION

1. Field of the Invention

The present invention relates to novel highly biolabile prodrug forms of drugs containing one or more carboxylic acid functions, to methods for preparing the prodrug forms, to pharmaceutical compositions containing such prodrug forms, and to methods for using the prodrug forms.

For purposes of this specification, the term "prodrug" denotes a derivative of a known and proven carboxylic acid functional drug (e.g. naproxen, L-dopa, salicylic acid, etc.) which derivative, when administered to warm-blooded animals, e.g. humans, is converted into the proven drug. The enzymatic and/or chemical hydrolytic cleavage of the compounds of the present invention occurs in such a manner that the proven drug form (parent carboxylic acid drug) is released, and the moiety or moieties split off remain nontoxic or are metabolized so that nontoxic metabolic products are produced.

These novel prodrug forms are esters of certain hydroxy-amides. These esters combine a high susceptibility to undergo enzymatic hydrolysis in vivo with a high stability in aqueous solution. The new ester prodrug type is further characterized by providing ample possibilities for varying the aqueous solubility as well as the lipophilicity of the prodrug derivatives with retainment of a favourable enzymatic/non-enzymatic hydrolysis index.

2. Description of the Prior Art

It is well-known that a wide variety of compounds containing carboxylic acid functions are biologically active. For example, such structure is characteristic of non-steroidal anti-inflammatory agents such as naproxen, ibuprofen, indomethacin and the like; penicillin and cephalosporin antibiotics such as ampicillin, cefmetazole and the like; as well as other compounds having diverse biological properties and structures.

It is also well-known that such prior art compounds are characterized by certain inherent disadvantages, notably bioavailability problems upon administration via oral, rectal or topical routes. The unionized form of a drug is usually absorbed more efficiently than its ionic species and as the carboxylic acid functional group is significantly ionized at physiological pH, the result is that carboxylic acid agents are poorly absorbed through lipid-water membrane barriers. In addition, by suffering from reduced bioavailability, some acidic drugs, notably non-steroidal anti-inflammatory agents (ibuprofen, tolmetin, naproxen, indomethacin, etc.), are irritating to the mucous membrane of the gastro-intestinal tract.

A promising approach to solve such problems may be esterification of the carboxylic acid function to produce lipophilic and non-irritating prodrug forms, provided that the biologically active parent drug can be released from the prodrug form at its sites of activity. However, several aliphatic or aromatic esters of carboxylic acid drugs are not sufficiently labile in vivo to ensure a sufficiently high rate and extent of prodrug conversion. For example, simple alkyl and aryl esters of penicillins are not hydrolyzed to active free penicillin acid in vivo (Holysz & Stavely, 1950) and therefore have no therapeutic potential (Ferres, 1983). Similarly, the much reduced anti-inflammatory activity observed for the methyl or ethyl esters of naproxen (Harrison et al., 1970) and fenbufen (Child et al., 1977) relative to the free acids may be ascribed to the resistance of the esters to be hydrolyzed in vivo. In the field of angiotensin-converting enzyme inhibitors ethyl esters have been developed as prodrugs for the parent active carboxylic acid drugs in order to improve their oral bioavailability. Enalapril is such a clinically used ethyl ester prodrug of enalaprilic acid. Plasma enzymes do not hydrolyze the ester and the necessary conversion of the ester to the free acid predominantly takes place in the liver (Tocco et al., 1982; Larmour et al., 1985). As recently suggested (Larmour et al., 1985), liver function may thus be a very important determinant for the bioactivation of enalapril and hence its therapeutic effect. The limited susceptibility of enalapril to undergo enzymatic hydrolysis in vivo has been shown to result in incomplete availability of the active parent acid (Todd & Heel, 1986). Pentopril is another ethyl ester prodrug of an angiotensin-converting enzyme inhibitor which also is highly stable in human plasma. In this case less than 50% of an oral dose of the prodrug ester appears to be deesterified in vivo to the active parent acid (Rakhit & Tipnis, 1985).

As has been demonstrated in the case of penicillins (Ferres, 1983) these shortcomings of some ester prodrugs may be overcome by preparing a double ester type, acyloxyalkyl or alkoxycarbonyloxyalkyl esters, which in general show a higher enzymatic lability than simple alkyl esters. The general utility of this double ester concept in prodrug design is, however, limited by the poor water solubility of the esters of several drugs and the limited stability of the esters in vitro. In addition, such esters are oils in many cases, thus creating pharmaceutical formulation problems.

In view of the foregoing, it is quite obvious that a clear need exists for new ester prodrug types possessing a high susceptibility to undergo enzymatic hydrolysis in plasma or blood and further more being characterized by providing ample possibilities for varying or controlling the water and lipid solubilities.

In accordance with the present invention it has now been discovered that esters of the formula I below are surprisingly rapidly cleaved enzymatically in vivo, e.g. by plasma enzymes, and fulfil the above-discussed desirable attributes.

A few compounds related to certain compounds of formula I have been reported in the literature. Thus, Boltze et al. (1980) have described various N-unsubstituted and N-monosubstituted 2-[1-(p-chlorobenzoyl)-5-methoxy-2-methylindole-3-acetyloxy]-acetamide derivatives having anti-inflammatory properties. Similarly, some acetamide derivatives of flufenamic acid have been reported by Boltze & Kreisfeld (1977). 2-[2-(Acetyloxy)benzoyloxy]-acetamide and other related ester derivatives of acetylsalicylic acid are disclosed in Ger. Offen. 2,320,945.

However, there is no suggestion that the compounds described have any prodrug activity, and enzymatic hydrolysis of the compounds into the parent carboxylic acid drugs is neither explicitly nor implicitly mentioned.

SUMMARY OF THE INVENTION

It is an object of the present invention to provide a novel ester prodrug type characterized by possessing a high susceptibility to undergo enzymatic hydrolysis in vivo and at the same time providing ample possibilities for varying the water and lipid solubilities of the derivatives.

It is another object of the present invention to provide novel bioreversible derivatives for drugs or biologically active agents having a carboxylic acid function which derivatives, when administered to warm-blooded animals, e.g. humans, elicit the bio-affecting/pharmacological response characteristic of the acids from which they are derived, yet which are characterized in being less irritating to topical and gastric or intestinal mucosal membranes.

It is another object of this invention to provide prodrugs of carboxylic acid agents which are capable of providing increased biomembrane transport so that the parent drugs are more bioavailable from the site of administration such as the gastro-intestinal tract, the rectum, the skin or the eye of the human body.

It is a further object of the present invention to provide such derivatives of conventional carboxylic acids which are prodrugs designed to cleave in such a manner as to enable the original parent drug form to be released at its therapeutic site or sites of activity, while the remaining cleaved moiety is non-toxic and/or is metabolized in a nontoxic fashion.

It is still another object of this invention to provide prodrug compounds which utilize hydrolytic enzymes to generate the parent carboxylic acid-type drug from the prodrug form.

It is yet another object of the present invention to provide derivatives of carboxylic acid agents which derivatives are "soft" in nature, i.e., which are characterized by in vivo destruction to essentially non-toxic moieties, after they have achieved their desired therapeutic role (for example, the compounds derived from steroidal acids of formula II below).

Other objects, features and advantages of the invention will be apparent to those skilled in the art from the detailed description of the invention which follows.

The foregoing objects, features and advantages are provided by the novel compounds of the formula I $$R-COO-(CH_2)_n-\overset{O}{\overset{\|}{C}}-N\overset{R_1}{\underset{R_2}{\diagdown}} \qquad I$$

wherein R—COO— represents the acyloxy residue of a carboxylic acid drug or medicament, n is an integer from 1 to 3, and $R_1$ and $R_2$ are the same or different and are selected from a group consisting of an alkyl group, an alkenyl group, an aryl group, an aralkyl group, a cycloalkyl group, in which the alkyl, alkenyl, aryl, aralkyl or cycloalkyl group is unsubstituted or substituted with one or more substituents selected from:
a halogen atom,
a hydroxy group,
a carbonyl group,
a straight or branched-chain alkoxy group having the formula $R_3$—O—, wherein $R_3$ represents an alkyl group or an aryl group, which groups may be unsubstituted or substituted with one or more of a halogen atom or a hydroxy group,
a carbamoyl group having the formula $$-CON\overset{R_5}{\underset{R_4}{\diagdown}},$$

wherein $R_4$ and $R_5$ are the same or different and are hydrogen, an alkyl group or are selected from a group having the formula —$CH_2NR_7R_6$, wherein $R_6$ and $R_7$ are the same or different and are hydrogen, an alkyl group, or together with the adjacent nitrogen atom form a 4-, 5-, 6- or 7-membered heterocyclic ring, which in addition to the nitrogen may contain one or two further heteroatoms selected from the group consisting of nitrogen, oxygen, and sulfur, an amino group having the formula —$NR_8R_9$, wherein $R_8$ and $R_9$ are the same or different and are hydrogen, an alkyl group or together with the adjacent nitrogen atom form a 4-, 5-, 6- or 7-membered heterocyclic ring, which in addition to the nitrogen may contain one or two further heteroatoms selected from the group consisting of nitrogen, oxygen, and sulfur, an acyloxy group having the formula —$COOR_{10}$, wherein $R_{10}$ is an alkyl, aryl or aralkyl group, an oxyacyl group having the formula $R_{11}COO$— wherein $R_{11}$ is hydrogen, an alkyl group, an aryl group, an aralkyl group, a cycloalkyl group, in which the alkyl, aryl, aralkyl or cycloalkyl group is unsubstituted or substituted with one or more of halogen atom, a hydroxy group, an alkoxy group of the formula $R_3$—O— as defined above, a carbamoyl group of the formula —$CONR_4R_5$ as defined above or an amino group having the formula —$NR_8R_9$ as defined above;

or $R_1$ and $R_2$ are combined so that —$NR_1R_2$ forms a 4-, 5-, 6- or 7-membered heterocyclic ring, which in addition to the nitrogen atom may contain one or two further heteroatoms selected from the group consisting of nitrogen, oxygen, and sulfur, and which heterocyclic ring may be substituted with a hydroxy group, a carbonyl group, an alkyl group or an oxyacyl group having the formula $R_{11}COO$—, wherein $R_{11}$ is as defined above, or an acyloxy group having the formula —$COOR_{10}$, wherein $R_{10}$ is as defined above;

and nontoxic pharmaceutically acceptable acid addition salts thereof, with the proviso that if $R_1$=alkyl then $R_2$=alkyl, and if $R_1$=$CH_2CH_2OH$ then $R_2$=$CH_2CH_2OH$.

In the present context, the term "alkyl" designates $C_{1-8}$ alkyl which may be straight or branched, such as methyl, ethyl, propyl, isopropyl, butyl, tert-butyl, pentyl, hexyl, heptyl, or octyl. The term "alkenyl" designates a $C_{2-6}$-monounsaturated aliphatic hydrocarbon group which may be straight or branched, such as propenyl, butenyl or pentenyl. The term "aryl" encompasses aryl radicals such as phenyl and naphthyl and also the corresponding aryl radicals containing one or more substitutents, which may be the same or different, such as alkylthio, alkyl, halogen, alkoxy, nitro, alkanoyl, carbalkoxy, dialkylamino, alkanoyloxy or hydroxy groups. The term "cycloalkyl" designates a radical containing 4 to 7 carbon atoms, e.g. cyclohexyl. The term "aralkyl" designates a radical of the type -alkylene-aryl, wherein aryl is as defined above and the alkylene moiety contains 1 to 6 carbon atoms and can be straight or branched-chain, e.g. methylene, 1,2-butylene, and the like. When $R_1$ and $R_2$ in the formula I, $R_4$ and $R_5$ in the formula —$CONR_4R_5$ and $R_8$ and $R_9$ in the formula —$NR_8R_9$ together with the adjacent nitrogen atom form a 4-, 5-, 6- or 7-membered heterocyclic ring which in addition to the nitrogen atom may contain 1 or 2 further hetero atoms selected from the group consisting of nitrogen, oxygen, and sulfur, it may, for instance, be 1-piperidinyl, 1-pyrrolidinyl, 1-piperazinyl, 4-methyl 1-piperazinyl, hexamethyleneimino, morpholinyl, thiomorpholinyl, 1-pyrazolyl and 1-imidazolyl.

When one or more asymmetric carbon atoms are present in the $R_1$ or $R_2$ groups as defined above, it is understood that the present invention also encompasses all diastereomers or enantiomers, or mixtures thereof. Examples of isomers are D-, L-, and DL- forms.

The term "non-toxic pharmaceutically acceptable acid addition salts" as used herein generally includes the non-toxic acid addition salts of compounds of formula I, formed with non-toxic inorganic or organic acids. For example, the salts include those derived from inorganic acids such as hydrochloric, hydrobromic, sulphuric, sulphamic, nitric, phosphoric and the like; and the salts with organic acids such as acetic, propionic, succinic, fumaric, maleic, tartaric, citric, glycolic, lactic, stearic, malic, pamoic, ascorbic, phenylacetic, benzoic, glutamic, salicylic, sulphuric, sulphanilic, and the like.

As stated above, R—COO— in formula I can represent the acyloxy residue of any drug, pharmaceutical or medicament (R—COOH) having one or more carboxylic acid functions. The chemical structure of the carboxylic acid agents is not critical. Examples of drugs or pharmaceuticals from which the instant prodrugs are derived include but are not limited to:

a. Non-steroidal anti-inflammatory agents like:
 1. Acetylsalicylic acid (aspirin)
 2. Salicylic acid
 3. Sulindac
 4. Indomethacin
 5. Naproxen
 6. Fenoprofen
 7. Ibuprofen
 8. Ketoprofen
 9. Indoprofen
 10. Furobufen
 11. Diflunisal
 12. Tolmetin
 13. Flurbiprofen
 14. Diclofenac
 15. Mefenamic acid
 16. Flufenamic acid
 17. Meclofenamic acid
 18. Fenclozic acid
 19. Alclofenac
 20. Bucloxic acid
 21. Suprofen
 22. Fluprofen
 23. Cinchophen
 24. Pirprofen
 25. Oxoprozin
 26. Cinmetacin
 27. Acemetacin
 28. Ketorolac
 29. Clometacin
 30. Ibufenac
 31. Tolfenamic acid
 32. Fenclofenac
 33. Prodolic acid
 34. Clonixin
 35. Flutiazin
 36. Flufenisal
 37. Salicylsalicylic acid
 38. O-(Carbamoylphenoxy)acetic acid
 39. Zomepirac
 40. Nifluminic acid
 41. Lonazolac
 42. Fenbufen
 43. Carprofen
 44. Tiaprofenic acid
 45. Loxoprofen
 46. Etodolac
 47. Alminoprofen
 48. 2-(8-Methyl-10,11-dihydro-11-oxodibenz[b,f]oxepin-2-yl)-propionic acid
 49. 4-Biphenylacetic acid b. Cephalosporin antibiotics like:
 100. Cephalothin
 101. Cephacetrile
 102. Cephapirin
 103. Cephaloridine
 104. Cefazolin
 105. Cefazuflur
 106. Ceforanide
 107. Cefazedone
 108. Ceftezole
 109. Cephanone
 110. Cefotiam
 111. Cefamandole
 112. Cefonicid
 113. Cefuroxime
 114. Cefoperazone
 115. Cefpiramide
 116. Cefpimizole
 117. Cefsulodin
 118. Cefoxitin
 119. Cefmetazole
 120. Cefotetan
 121. Cefbuperazone
 122. Cefotaxime
 123. Cefmenoxime
 124. Ceftizoxime
 125. Cefpirome
 126. Ceftazidime
 127. Cefodizime
 128. Ceftriaxone
 129. Latamoxef
 130. Cephalexin
 131. Cephradine
 132. Cefaclor
 133. Cefadroxil
 134. Cefatrizine
 135. Cefroxadine
 136. Cephaloglycin c. Penicillin antibiotics like:
 200. Benzylpenicillin
 201. Phenoxymethylpenicillin
 202. Phenethicillin
 203. Methicillin
 204. Nafcillin
 205. Oxacillin
 206. Cloxacillin
 207. Dicloxacillin
 208. Flucloxacillin
 209. Azidocillin 210. Ampicillin
211. Amoxycillin
212. Epicillin
213. Cyclacillin
214. Carbenicillin
215. Ticarcillin
216. Sulbenicillin
217. Azlocillin
218. Mezlocillin
219. Piperazillin
220. Apalcillin
221. Temocillin
222. Carfecillin
223. Carindacillin
224. Hetacillin d. 4-Quinolone antibiotics like:
300. Ciprofloxacin
301. Norfloxacin
302. Acrosoxacin
303. Pipemidic acid
304. Nalidixic acid
305. Enoxacin
306. Ofloxacin
307. Oxolinic acid
308. Flumequine
309. Cinoxacin
310. Piromidic acid
311. Pefloxacin e. Steroidal monocarboxylic acids having the structural formula II:

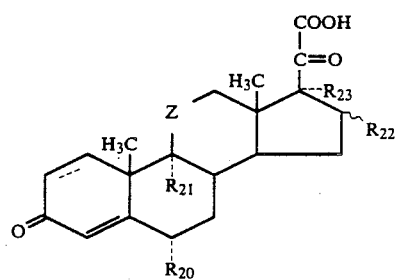

H wherein $R_{20}$ is hydrogen, fluoro, chloro, or methyl; $R_{21}$ is hydrogen, fluoro or chloro; $R_{22}$ is hydrogen, methyl, hydroxy or —$OCOR_{24}$ wherein $R_{24}$ is $C_1$–$C_7$ straight or branched alkyl or phenyl; $R_{23}$ is hydrogen, hydroxy, or —$OCOR_{24}$ wherein $R_{24}$ is as defined above, with the proviso that when $R_{22}$ is hydroxy or —$OCOR_{24}$ and $R_{23}$ is other than hydrogen, then $R_{22}$ and $R_{23}$ are identical; or $R_{22}$ and $R_{23}$ are combined to form a divalent radical of the type

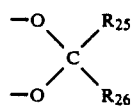 III wherein $R_{25}$ and $R_{26}$, which can be the same or different are each $C_{1-7}$ straight or branched alkyl or phenyl; Z is carbonyl or β-hydroxymethylene; the wavy line at the 16-position indicates the α or β-configuration; and the dotted line in the ring A indicates that the 1,2-linkage is saturated or unsaturated.

A particularly preferred group of carboxylic acids of the formula II consists of the compounds wherein the structural variables represented by $R_{20}$, $R_{21}$, $R_{22}$, $R_{23}$ and Z and the dotted and wavy lines are identical to those of a known anti-inflammatory steroid selected from the group consisting of hydrocortisone, betamethasone, dexamethasone, prednisolone, triamcinolone, fluocortolone, cortisone, fludrocortisone, chloroprednisone, flumethasone, fluprednisolone, meprednisone, methyl prednisolone, paramethasone, prednison, flurandrenolone acetonide, amcinafal, amcinafide, clocortolone, desonide, desoximetasone, fifluprednate, flunisolide, fluocinolone acetonide. triamcinolone acetonide, betamethasone 17-benzoate and betamethasone 17-valerate. Another preferred group of compounds of formula II consists of the compounds wherein the structural variables represented by $R_{20}$, $R_{21}$, $R_{22}$, Z and the dotted and wavy lines are identical to those of a known anti-inflammatory steroid selected from the group consisting of hydrocortisone, cortisone, fludrocortisone, betamethasone, chloroprednisone, dexamethasone, flumethasone, fluprednisolone, meprednisone, methyl prednisolone, paramethasone and prednisolone, and $R_{23}$ is —$OCOR_{24}$ wherein $R_{24}$ is as hereinbefore defined, most especially when $R_{24}$ is $CH_3$, $C_2H_5$, $C_3H_7$ or phenyl. Yet another preferred group of parent acids of formula II consists of the compounds wherein the structural variables represented by $R_{20}$, $R_{21}$, Z and the wavy and dotted lines are identical to those of triamcinolone, and $R_{22}$ and $R_{23}$ are identical —$OCOR_{24}$ groupings wherein $R_{24}$ is as hereinbefore defined, most especially when $R_{24}$ is $CH_3$, $C_2H_5$, $C_3H_7$ or phenyl. Particularly preferred parent acids encompassed by formula II include 6α-fluoro-11β-hydroxy-16α-methyl-3,20-dioxopregna-1,4-dien-21-oic acid;
9α-fluoro-11β,17α-dihydroxy-16β-methyl-3,20-dioxopregna-1,4-dien-21-oic acid;
9α-fluoro-11β,17α-dihydroxy-16α-methyl-3,20-dioxopregna-1,4-dien-21-oic acid;
11β,17α-dihydroxy-3,20-dioxopregn-4-en-21-oic acid;
9α-fluoro-11β,16α,17α-trihydroxy-3,20-dioxopregna-1,4-dien-21-oic acid; and
11β,17α-dihydroxy-3,20-dioxopregna-1,4-dien-21-oic acid;

as well as the corresponding 17-esters of the specific 17-hydroxy compounds just named, most especially the 17-propionates, butyrates and benzoates thereof.

f. Prostaglandins like:
500. Prostaglandin $E_2$
501. Prostaglandin $F_{2\alpha}$
502. 15-Deoxy-16-hydroxy-16-vinylprostaglandin $E_2$
503. 11-Deoxy-11α,12α-methanoprostaglandin $E_2$
504. 11-Deoxy-11α,12α-difluoromethanoprostaglandin $E_2$
405. Prostacyclin
506. Epoprostenol
507. dl-16-Deoxy-16-hydroxy-16 (α/β)-vinyl prostaglandin $E_2$
508. Prostaglandin $E_1$
509. Thromboxane $A_2$
510. 16,16-Dimethylprostaglandin $E_2$
511. (15R) 15-Methylprostaglandin $E_2$ (Arbaprostil)
512. Meteneprost
513. Nileprost
514. Ciprostene g. Angiotensin-converting enzyme inhibitors like:

600. (2R, 4R)-2-(2-Hydroxyphenyl)3-(3-mercapto-propionyl)-4-thiazolidinecarboxylic acid
601. Enalaprilic acid (N-[1-(S)-carboxy-3-phenyl-propyl]-L-alanyl-L-proline)
602. Captopril
603. N-Cyclopentyl-N-[3-[(2,2-dimethyl-1-oxo-propyl)thio]-2-methyl-1-oxopropyl]glycine
604. 1[4-Carboxy-2-methyl-2R,4R-pentanoyl]-2,3-dihydro-2S-indole-2-carboxylic acid
605. Alecapril (1-[(S)-3-Acetylthio-2-methyl-propanoyl]-L-propyl-L-phenylalanine)
606. [3S-[2[R*(R*)]],3R*]-2-[2-[[1-carboxy-3-phenyl-propyl]-amino]-1-oxopropyl]-1, 2,3,4-tetrahydro-3-isoquinoline carboxylic acid
607. [2S-[1[R*(R*)]],2α,3αβ, 7αβ]-1[2-[[1-carboxy-3-phenylpropyl]-amino]-1-oxopropyl]octahydro-1H-indole-2-carboxylic acid.
608. (S)-Benzamido-4-oxo-6-phenylhexanoyl-2-car-boxy-pyrrolidine
609. Lisinopril
610. Tiopronin
611. Pivopril h. Various other bio-affecting carboxylic acid agents:
700. Ethacrynic acid
701. L-Tyrosine
702. α-Methyl-L-tyrosine
703. Penicillamine
704. Probenicid
705. 5-Aminosalicylic acid
706. 4-Aminobenzoic acid
707. Methyldopa
708. L-Dopa
709. Carbidopa
710. Valproic acid
711. 4-Aminobutyric acid
712. Moxalactam
713. Clavulanic acid
714. Tranexamic acid
715. Furosemide
716. 7-Theophylline acetic acid
717. Clofibric acid
718. Thienamycin
719. N-Formimidoylthienamycin
720. Amphotericin B
721. Nicotinic acid
722. Methotrexate
723. L-Thyroxine
724. Cromoglycic acid
725. Bumetanide
726. Folic acid
727. Chlorambucil
728. Melphalan
729. Fusidic acid
730. 4-Aminosalicylic acid
731. Liothyronine
732. Tretinoin
733. o-Thymotinic acid
734. 6-Aminocaproic acid
735. L-Cysteine
736. Tranilast (N-(3',4'-dimethoxycinnamoyl)an-thranilic acid)
737. Baclofen
738. 4-Amino-5-ethyl-3-thiophenecarboxylic acid
739. N-Cyclopentyl-N-[3-[(2,2-dimethyl-1-oxo-propyl)thio]2-methyl-1-oxopropyl]glycine
740. Isoguvacine
741. Nipecotic acid
742. D-Eritadenine [(2R,3R)-4-adenin-9-yl-2,3-dihy-droxybutanoic acid]
743. (RS)-3-Adenin-9-yl-2-hydroxypropanoic acid
744. 1-[4-Carboxy-2-methyl-2R,4R-pentanoyl]-2,3-dihydro-2S-indole-2-carboxylic acid
745. Phenylalanylalanine
746. Glafenic acid
747. Floctafenic acid
748. N-(Phosphonoacetyl)-L-aspartic acid (PALA)
749. Proxicromil
750. Cysteamine
751. N-Acetylcysteine
752. Proglumide
753. Aztreonam
754. Mecillinam
755. All-trans-retinoic acid
756. 13-cis-retinoic acid
757. Isonipecotic acid
758. Anthracene-9-carboxylic acid
759. α-Fluoromethylhistidine
760. 6-Amino-2-mercapto-5-methylpyrimidine-4-car-boxylic acid
761. Glutathione
762. Acivicin
763. L-α-Glutamyl dopamine
764. 6-Aminonicotinic acid
765. Loflazepate
766. 6-[[1(S)-[3(S),4-dihydro-8-hydroxy-1-oxo-1 H-2-benzopyran-3-yl]-3-methylbutyl]amino]-4-(S),5(S)-dihydroxy-6-oxo-3(S)-ammoniohexanoate
767. Z-2-Isovaleramidobut-2-enoic acid
768. D,L-2,4-Dihydroxyphenylalanine
769. L-2-Oxothiazolidine-4-carboxylic acid
770. Iopanoic acid
771. 4-Aminomethylbenzoic acid
772. 4-Hydroxybenzoic acid
773. 4-Hydroxybutyric acid
774. Ticrynafen
775. 4-amino-3-phenylbutyric acid
776. 4-(Dimethylamino)benzoic acid
777. Capobenic acid
778. Pantothenic acid
779. Folinic acid
780. Orotic acid
781. Biotin
782. Mycophenolic acid
783. Thioctic acid
784. Pyroglutamic acid
785. Oleic acid
786. Linoleic acid
787. Cholic acid
788. Naturally occurring amino acids (e.g. glycine, histidine, phenylalanine and glutamic acid)
789. N,N-Dimethylglycine
790. Salazosulfapyridine
791. Azodisal
792. Isotretinoin
793. Etretinic acid All of the above compounds are known in the art in the acid or salt form.

While all of the compounds encompassed by formula 1 essentially satisfy the objectives of the present invention, preferred compounds include those derived from the following compounds (compounds A)
1. Acetylsalicylic acid
2. Salicylic acid
3. Sulindac
4. Indomethacin 5. Naproxen
7. Ibuprofen
8. Ketoprofen
11. Diflunisal
12. Tolmetin
13. Flurbiprofen
15. Mefenamic acid
21. Suprofen
31. Tolfenamic acid
119. Cefmerazole
104. Gefazolin
130. Cephalexin
132. Cefaclor
133. Cefuroxime
134. Cefamandole
118. Cefoxitin
200. Benzylpenicillin
201. Phenoxymethylpenicillin
210. Ampicillin
211. Amoxycillin
214. Carbenicillin
217. Azlocillin
219. Piperacillin
6α-Fluoro-11β-hydroxy-16α-methyl-3,20-dioxopregna-1,4-dien-21-oic acid
9α-Fluoro-11β,17α-dihydroxy-16β-methyl-3,20-dioxopregna-1,4-dien-21-oic acid
9α-Fluoro-11β,17α-dihydroxy-16α-methyl-3,20-dioxopregna-1,4-dien-21-oic acid
11β,17α-Dihydroxy-3,20-dioxopregn-4-en-21-oic acid
9α-Fluoro-11β,16α,17α-trihydroxy-3,20-dioxopregna-4-dien-21-oic acid
11β,17α-Dihydroxy-3,20-dioxopregna-1,4-dien-21-oic acid.
500. Prostaglandin E₂
501. Prostaglandin F₂α
508. Prostaglandin E₁
505. Prostacyclin
511. (15R)-15-Methylprostaglandin E₂ (Arbaprostil)
513. Nileprost
514. Ciprostene
601. Enalaprilic acid
602. Captopril
603. N-Cyclopentyl-N-[3[(2,2-dimethyl-1-oxopropyl)thio]-2-methyl-1-oxopropyl]glycine
604. 1-[4-Carboxy-2-methyl-2R,4R-pentanoyl]-2,3-dihydro-2S-indole-2-carboxylic acid
607. [2S [1[R*(R*)]],2α,3αβ,7αβ]-1-[2-[[1-carboxy-3-phenylpropyl]amino]-1-oxopropyl]octahydro-1H-indole-2-carboxylc acid
705. 5-Aminosalicylic acid
707. Methyldopa
708. L-Dopa
710. Valproic acid
714. Tranexamic acid
715. Furosemide
722. Methotrexate
727. Chlorambucil
717. Clofibric acid
720. Amphotericin B
734. 6-Aminocaproic acid
754. Mecillinam
732. Tretinoin
771. 4-Aminomethylbenzoic acid
782. Mycophenolic acid
768. D,L-2,4-Dihydroxyphenylalanine Particularly preferred compounds of the invention include those wherein R—COO is derived from one of the specific bio-affecting acids named above, n is 1 and $R_1$ and $R_2$ are as defined in connection with the general formula I.

In especially preferred compounds of the formula I, R—COO is derived from one of the compounds A above, n=1, and
$R_1$=CH₃ or C₂H₅, and $R_2$ =
—CH₂CH₂OH
—CH₂CONH₂
—CH₂CH₂CONH₂
—CH₂CH₂OOCCH₂N(CH₃)₂
—CH₂CH₂OOCCH₂N(C₂H₅)₂
—CH₂CH₂OOCCH₂NH₂

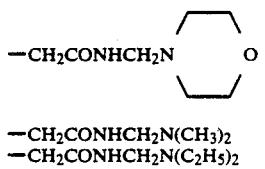

—CH₂CONHCH₂N(CH₃)₂
—CH₂CONHCH₂N(C₂H₅)₂

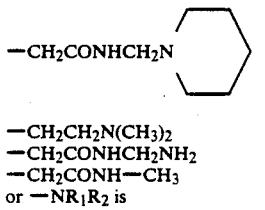

—CH₂CH₂N(CH₃)₂
—CH₂CONHCH₂NH₂
—CH₂CONH—CH₃
or —NR₁R₂ is

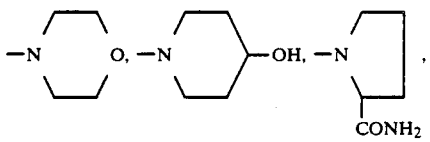

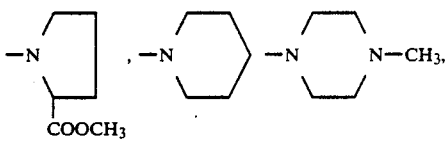

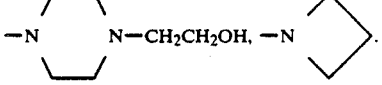

It will be appreciated that in the especially preferred compounds defined immediately above, each and every possible combination between the given examples of $R_1$ and $R_2$ in the derivative group —CH₂CONR₁R₂ may, of course, be combined with each and every group R—COO derived from the compounds A listed above, and that the above definition is equivalent to listing each and every possible combination of the listed examples of R—COO, $R_1$ and $R_2$.

The invention further concerns compounds of the general formula I as defined above wherein $R_1$ and $R_2$ both are alkyl or both are —CH₂CH₂OH, and R—COO— is the acyloxy residue of one of the following bio-affecting carboxylic acid agents (compounds B)
2. Salicylic acid
3. Sulindac
4. Indomethacin
5. Naproxen
7. Ibuprofen 8. Ketoprofen
11. Diflunisal
12. Tolmetin
13. Flurbiprofen
15. Mefenamic acid
21. Suprofen
31. Tolfenamic acid
119. Cefmetazole
104. Cefazolin
130. Cephalexin
132. Cefaclor
133. Cefuroxime
134. Cefamandole
118. Cefoxitin
200. Benzylpenicillin
201. Phenoxymethylpenicillin
210. Ampicillin
211. Amoxycillin
214. Carbenicillin
217. Azlocillin
219. Piperacillin 6α-Fluoro-11β-hydroxy-16α-methyl-3,20-dioxopregna-1,4-dien-21-oic acid 9α-Fluoro-11β,17α-dihydroxy-16β-methyl-3,20-dioxopregna-1,4-dien-21-oic acid 9α-Fluoro-11β,17α-dihydroxy-16α-methyl-3,20-dioxopregna-1,4-dien-21-oic acid 11β,17α-Dihydroxy-3,20-dioxopregn-4-en-21-oic acid 9α-Fluoro-11β,16α,17α-trihydroxy-3.20-dioxopregna-4-dien-21-oic acid 11β,17α-Dihydroxy-3,20-dioxopregna-1,4-dien-21-oic acid.

500. Prostaglandin $E_2$
501. Prostaglandin $F_{2\alpha}$
508. Prostaglandin $E_1$
505. Prostacyclin
511. (15R)15-Methylprostaglandin $E_2$ (Arbaprostil)
513. Nileprost
514. Ciprostene
601. Enalaprilic acid
602. Captopril
603. N-Cyclopentyl-N-[3-[(2,2-dimethyl-1-oxopropyl)thio]-2-methyl-1-oxopropyl]glycine
604. 1-[4-Carboxy-2-methyl-2R,4R-pentanoyl]-2,3-dihydro-2S-indole-2-carboxylic acid
607. [2S-[1[R*(R*)]],2α,3αβ,17αβ]-1-[2-[[1-carboxy-3-phenylpropyl]amino]-1-oxopropyl]octahydro-1H-indole-2-carboxylic acid
705. 5-Aminosalicylic acid
707. Methyldopa
708. L-Dopa
710. Valproic acid
714. Tranexamic acid
715. Furosemide
722. Methotrexate
727. Chlorambucil
717. Clofibric acid
720. Amphotericin B
734. 6-Aminocaproic acid
754. Mecillinam
732. Tretinoin
771. 4-Aminomethylbenzoic acid
782. Mycophenolic acid
768. D,L-2,4-Dihydroxyphenylalanin When $R_1$ and $R_2$ are both alkyl, they may be the same or different and are preferably $C_{1-3}$ alkyl such as methyl, ethyl, n-propyl or isopropyl. It is further preferred that n=1. It will be appreciated that in such preferred compounds, each and every possible combination of $R_1$ and $R_2$ (i.e. both being —CH$_2$CH$_2$OH, or $R_1$ and $R_2$ individually being selected from methyl, ethyl, propyl and isopropyl) in the derivative group —CH$_2$CONR$_1$ R$_2$ may, of course, be combined with each and every group R—COO derived from the compounds B listed above, and that the above definition is equivalent to listing each and every possible combination of the listed examples of R—COO (from compounds B), $R_1$ and $R_2$.

DETAILED DESCRIPTION OF THE INVENTION

DOSAGE FORMS AND DOSE

The prodrug compounds of formula I of the present invention can be used to treat any condition for which the parent carboxylic group containing drug, medicament or pharmaceutical is useful. For example, if naproxen is the parent drug of choice, the ester prodrug can be used for any condition or treatment for which naproxen would be administered.

Thus, the prodrug compounds of formula I may be administered orally, topically, parenterally, rectally or by inhalation spray in dosage forms or formulations containing conventional, non-toxic pharmaceutically acceptable carriers, adjuvants and vehicles. The formulation and preparation of any of this broad spectrum of dosage forms into which the subject prodrugs can be disposed is well-known to those skilled in the art of pharmaceutical formulation. Specific information can, however, be found in the text entitled "Remington's Pharmaceutical Sciences", Sixteenth Edition, 1980.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide a pharmaceutically elegant and palatable preparation.

Formulations for oral use include tablets which contain the active ingredient in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

Aqueous suspensions usually contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, methyl, ethyl or n-propyl p-hydroxybenzoate; one or more colouring agents; one or more flavouring agents; and one or more sweetening agents such as sucrose or saccharin.

Oily suspension may be formulated by suspending the active ingredient in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. Sweetening agents such as those set forth above, and flavouring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavouring and colouring agents, may also be present.

The pharmaceutical compositions of the invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth; naturally-occurring phosphatides, for example, soybean licithin; and esters including partial esters derived from fatty acids and hexitol anhydrides, for example, sorbitan mono-oleate, and condensation products of the said partial esters with ethylene oxide, for example, polyoxyethylene sorbitan monooleate. The emulsions may also contain sweetening and flavouring agents.

Syrups and elixirs may be formulated with sweetening agents, for example glycerol, sorbitol or sucrose. Such formulations may also contain a· demulcent, a preservative and flavouring and colouring agents, The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may be a sterile injectable solution or suspension in a non-toxic parenterally acceptable diluent or solvent. Among the acceptable vehicles and solvents that may be employed are water, 1,3-butanediol, Ringer's solution and isotonic sodium chloride solution. In addition, sterile fixed oils are conventionally employed as a solvent or suspending medium. For this purpose any bland fixed oil may be employed including synthetic monoor diglycerides. Fatty acids such as oleic acid also find use in the preparation of injectibles.

The compounds of formula I may also be administered in the form of suppositories for rectal administration of the drug. These compositions can be prepared by mixing the drug with a suitable nonirritating excipient which is solid at ordinary temperatures but liquid at the rectal temperature and will therefore melt in the rectum to release the drug, for example, cocoa butter, or adeps solidus polyethylene glycols.

For topical use, creams, ointments, jellies, solutions, suspensions or the like containing the prodrugs are employed according to methods recognized in the art.

Naturally, therapeutic dosage range for the compounds of the present invention will vary with the size and needs of the patient and the particular pain or disease symptom being treated. However, generally speaking, the following dosage guidelines will suffice. On an oral basis, the therapeutic dose required for a compound of the present invention will generally, on a molecular basis, mimic that for the parent carboxylic acid drug. On a topical basis, application of an 0.01% to 5% concentration of a compound of the present invention (in a suitable topical carrier material) to the affected site should suffice.

From the foregoing description, one of ordinary skill in the art can easily ascertain the essential characteristics of the present invention and, without departing from the spirit and scope thereof, can make various changes and/or modifications of the invention to adapt it to various usages and conditions. As such, these changes and/or modifications are properly, equitably and intended to be within the full range of equivalence of the following claims.

The amount of active ingredient that may be combined with the carrier materials to produce a single dosage form will vary depending upon the host treated and the particular mode of administration. For example, a formulation intended for the oral administration of humans may contain from 5 mg to 5 gm of the active agent compounded with an appropriate and convenient amount of carrier material which may vary from about 5 to about 95% of the total composition. Other dosage forms such as ophthalmic dosage forms contain less active ingredient such as for example from 0.1 mg to 5 mg. Dosage unit forms will generally contain between from about 0.1 mg to about 500 mg of active ingredient.

It will be understood, however, that the specific dose level for any particular patient will depend upon a variety of factors including the activity of the specific compound employed, the age, body weight, general heath, sex, diet, time of administration, route of administration, rate of excretion, drug combination and severity of the particular disease undergoing therapy.

PREPARATION OF THE PRODRUGS OF FORMULA I

The compounds of the present invention can be prepared by a variety of synthetic routes. A generally applicable process (method a) comprises reacting the carboxylic acid agent of the formula A or a salt (e.g. a metal salt) thereof

R—COOH    (A)

wherein R—COO— is defined as above in connection with formula I, with a compound having the formula B:

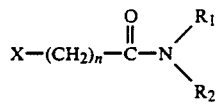    (B)

wherein n, $R_1$ and $R_2$ are as defined above and X is a suitable leaving group (e.g., halogen such as Cl, I or Br, or a methansulfonyloxy or toluenesulfonyloxy group). The reaction is preferably carried out in a solvent (e.g. N,N-dimethylformamide, water, acetonitrile, a lower alcohol, ethyl acetate, toluene or the like). An equivalent of an organic base such as triethylamine, tetramethylguanidine or the like is typically added or crown ethers are used as phase-transfer catalysts. If X in formula B is chlorine catalytic amounts of an iodide salt may be added to the reaction mixture. The reaction is carried out at a temperature of from room temperature to the boiling point of the solvent, and for a period of time of 0.5 to 48 hours.

Another method (method b) for preparing compounds of the invention comprises reacting a compound of the formula B, wherein X is hydroxy, with an acid of the formula A or with the corresponding acid chloride of the formula C R—COCl    (C)

When an acid starting material is used, i.e. a compound of formula A, the reaction is conducted in the presence of a suitable dehydrating agent, for example N,N-dicyclohexylcarbodiimide. The reaction utilizing an acid starting material is conveniently carried out in an inert solvent such as dichloromethane, dioxane, pyridine or the like, at a temperature of from 0° to 60° C., for from 1 to 48 h. A catalyst such as p-toluenesulphonic acid or 4-(N,N-dimethylamino)pyridine may be added. When the reaction utilizes an acid chloride starting material, the process can be conveniently carried out by reacting the compound of formula B, wherein X is hydroxy, with the desired acid chloride in an inert solvent such as benzene, dichloromethane, dimethylformamide, acetone, dioxane, acetonitrile or the like, at from room temperature to reflux, for from 1 to 24 h, in the presence of an acid scavenger such as an alkali metal carbonate, or an organic base such as triethylamine or pyridine.

The acid chlorides of formula C which can be used in the above method are prepared from the corresponding acids by known means. e.g. by treatment of the acid with thionyl chloride or oxalyl chloride. Instead of acid chlorides acid anhydrides or mixed anhydrides may be used.

The starting materials of formula B, in which X is a halogen, are also prepared by known means, e.g. by treatment of the appropriate amine with an appropriately halogen-substituted acid chloride, acid anhydride or ester as represented by the following chemical equation for an acid chloride:

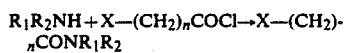

Several compounds of formula B, in which X is a halogen, and methods for their preparation, have been described in the literature, see e.g. Hankins (1965), Weaver and Whaley (1947), Ronwin (1953), Berkelhammer et al. (1961) and Speziale and Hamm (1956).

The starting materials of formula B, in which X is hydroxy, are also prepared by known means, e.g. by hydrolysis of 2-(acetoxymethyl)acetamides or 2-(benzoyloxymethyl)acetamides. Specific examples are given below.

Several compounds of formula B, in which X is hydroxy, and methods for their preparation, have been described in the literature, see e.g. DE Offen. 2,904,490, DE 2,201,432, and DE 2,219,923.

A third method (method c) for preparing compounds of the present invention comprises reacting a compound of the formula D $HNR_1R_2$    (D)

wherein $R_1$ and $R_2$ are as defined above in connection with formula I, with an acid of the formula E R—COO(CH)$_n$COOH    (E)

wherein R—COO— and n are as defined above in connection with formula I, or with the corresponding acid chloride (or acid anhydrides) of the formula F R—COO(CH$_2$)$_n$COCl    (F)

When a compound of formula E is used, the reaction is conducted in the presence of a suitable dehydrating agent, e.g. N,N-dicyclohexylcarbodiimide. The reaction is conveniently carried out in an inert solvent such as dichloromethane, dioxane, pyridine or the like, at a temperature of from 0° to 60° C., for from 1 to 48 h. When the reaction utilizes an acid chloride starting material of formula F, the process can be conveniently carried out by reacting the compound of formula F with the desired amine or amine salt in a solvent such as benzene, dichloromethane, dimethylformamide, acetone, dioxane, acetonitrile, water or the like, at from 0° C. to reflux, for from ½ to 24 h, in the presence of an acid scavenger such as alkali metal carbonate, or an organic base such as triethylamine, or an excess of the amine.

The acid chlorides of formula F which can be used in the above method are prepared from the corresponding acids by known means. e.g. by treatment of the acid with thionyl chloride or oxalyl chloride.

The acids of formula E which can be used in the above method are prepared from the parent acids (i.e. R—COOH) by known means, e.g. by reacting the acid or a salt of the acid (e.g. a metal or trimethylammonium salt) with compounds of the formula G X—(CH$_2$)$_n$COOCH$_2$C$_6$H$_5$    (G)

wherein X and n are as defined above, or with compounds of the formula H

X—(CH$_2$)$_n$CONH$_2$    (H)

wherein X and n are as defined above. The intermediates obtained therefrom, i.e. R—COO—(CH$_2$)$_n$COOCH$_2$C$_6$H$_5$ and R—COO—(CH$_2$)$_n$—CONH$_2$, are subsequently transformed to the compounds of formula E by e.g. hydrogenation or acidic hydrolysis. Several compounds of formula E and methods for preparing them are known from the literature, see e.g. Boltze et al. (1980) and Concilio & Bongini (1966).

While the basic methods described above can be used to prepare any of the compounds of the invention, certain conditions and/or modifications therein are made in specific instances. Thus, for example, the basic methods may be modified in the cases where the desired product of formula I contains free aliphatic amino, thiol or hydroxyl groupings which, if present in the acid starting material, would undergo undesired side reaction and/or would interfere with the desired course of the above-described ester formation. In such cases, the compounds of formula B or D are reacted with an acid of the formula J $$R^1\text{—COOH} \qquad (J)$$

wherein $R^1$—COO— is the amino-, thiol- or hydroxyl-protected acyloxy residue of a carboxylic acid agent (R—COOH) containing amino, thiol or hydroxyl groups. The amino, hydroxy or thiol function in the parent acids of the formula RCOOH are converted to their protected counterparts in formula J by known methods, e.g. those known in the art of peptide synthesis. For example, amino groups are conveniently protected by the carbobenzoxycarbonyl or t-butyloxycarbonyl group. The compound of formula J, its corresponding acid chloride or protected counterpart for formula E is subsequently reacted with a compound of formula B or D, as described supra, to afford the compound corresponding to formula I, but containing a protected acyloxy residue, i.e. $R^1$—COO— as defined above in place of R—COO— in formula I. That protected compound is then deprotected by known methods, e.g. by hydrogenation or hydrolysis.

The above-described process variations involving the addition and ultimate removal of protecting groups is only used when the free amino, hydroxy and/or thiol functions are in need of protection.

When the starting acid of formula I hereinabove is a steroidal acid of formula II, this can be prepared by methods known in the art, for example by the methods described in U.S. Pat. No. 4,164,504 (Varma). See also *Chemical Abstracts*, 83, 179407 and 84, 122146. Thus, the following reaction scheme is illustrative of a general method for preparing the desired acids:

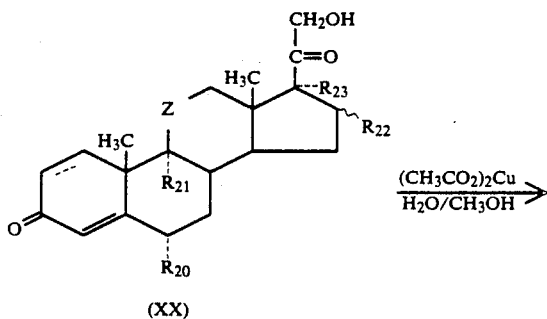

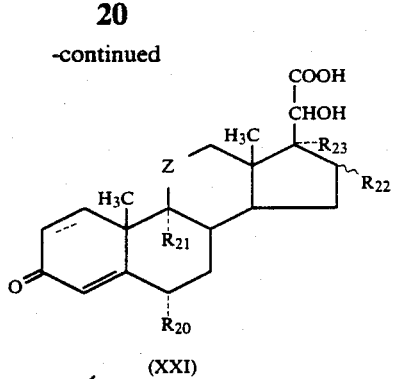

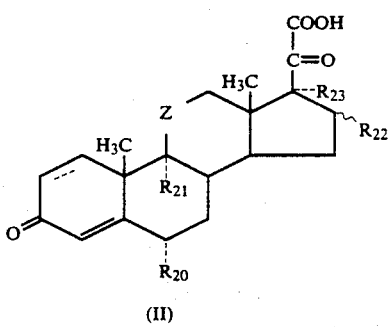

wherein $R_{20}$, $R_{21}$, $R_{22}$, $R_{23}$, Z and the dotted and wavy lines are defined as before. In the cupric acetate reaction, water is used as a co-solvent with a suitable alcohol, e.g. methanol or other lower alkanol, and the reaction is allowed to proceed for an extended period of time (more than 24 hours), since decreasing the water present and lessening reaction time tend to favour formation of the 21-ester of the steroid with the alcohol employed. Also, oxygen or air is bubbled through the mixture during the course of the reaction to encourage formation of 21-acid rather than 21-aldehyde. In the second step, the 20-hydroxy group is oxidized to a 20-keto function by reacting the steroid of formula XXI with manganese dioxide or lead dioxide in an inert halogenated hydrocarbon solvent such as chloroform or dichloromethane.

Figure 1:
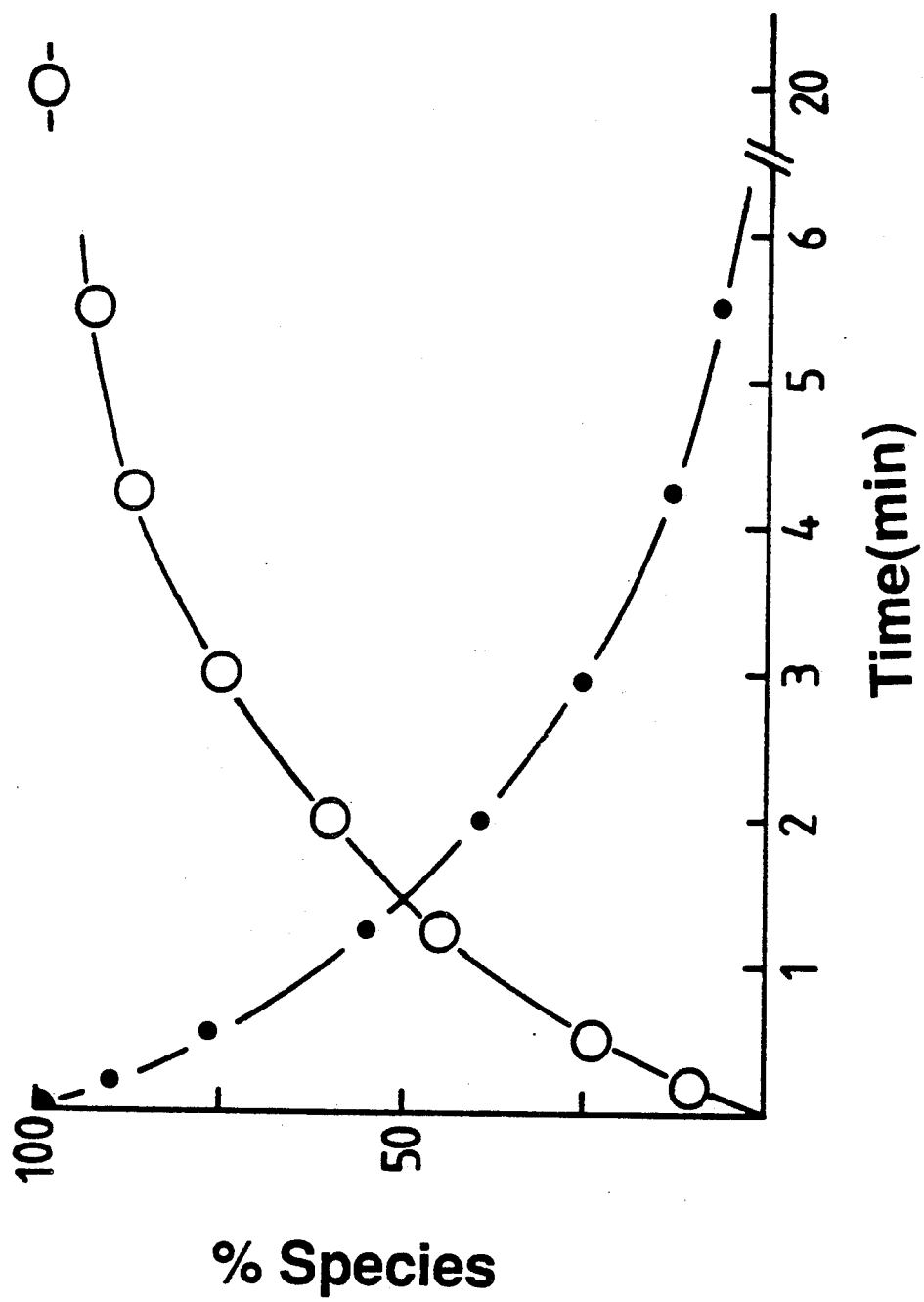
FIG. 1 shows time courses for naproxen N,N-dimethylglycolamide ester (●) and naproxen (O) during hydrolysis of the ester in 80% human plasma at 37° C. The initial ester concentration was $10^{-4}$M.

the present invention is further illustrated by the following examples which, however, are not construed to be limiting. The derivatives described all had spectroscopic properties (IR and $^1$H NMR) and elemental analysis (C, H and N) in agreement with their structures.

EXAMPLE 1

2(BENZOYLOXY)-N,N-DIMETHYLACETAMIDE

Benzoic acid (2.44 g, 0.02 mole) and 2-chloro-N,N-dimethylacetamide (2.43 g, 0.02 mole) were dissolved in 10 ml of N,N-dimethylformamide. Sodium iodide (150, 2 mmol) and triethylamine (2.02 g, 0.02 mole) were added and the mixture was stirred at room temperature (20°-25° C.) overnight. After addition of 50 ml of water the reaction mixture was extracted twice with ethyl acetate. The combined extracts were washed with a diluted solution of sodium thiosulphate, a 2% aqueous solution of sodium bicarbonate, water, dried over anhydrous sodium sulphate and evaporated in vacuo. The residue was crystallized from ethanol-water to give 3.5 g (85%) of the title compound. Mp 81°-82° C.

EXAMPLE 2

The compound in Example 1 was also prepared by the following procedure:

2-Chloro-N,N-dimethylacetamide (12.16 g, 0.1 mole) was added to a solution of sodium benzoate (14.4 g, 0.1 mole) and sodium iodide (3.75 g, 0.025 mole) in 75 ml of water. The reaction solution was refluxed for 2 h. Upon standing overnight at 4° C. the title compound precipitated. It was filtered off, washed with water and recrystallized from aqueous ethanol (15.7 g; 76%). Mp 83°-82° C.

EXAMPLE 5

(BENZOYLOXY)ACETYL CHLORIDE

2-Chloroacetamide (18.7 g, 0.2 mole) was added to a solution of sodium benzoate (28.8 g, 0.2 mole) and sodium iodide (7.5 g, 0.05 mole) in 150 ml of water. The mixture was stirred at 90° C. for 14 h.

Upon cooling to 4° C. 2-(benzoyloxy)acetamide precipitated and was isolated by filtration. Recrystallization from ethanol-water yielded 32.2 g (90%). Mp 120.5°-121° C.

2-(Benzoyloxy)acetamide (19.7 g, 0.11 mole) was added to 200 ml of 7.8M hydrochloric acid. The mixture was stirred at 75° C. for 10 min. Upon cooling 2-(benzoyloxy)acetic acid precipitated. It was isolated by filtration, dried and recrystallized from benzene (15.8 g, 80%), M. 111°-112° C.

A mixture of 2-(benzoyloxy)acetic acid (12.6 g) and thionyl chloride (15 ml) was refluxed for 3 h. Excess of thionyl chloride was removed in vacuo and the crude (benzoyloxy)acetyl chloride obtained was purified by distillation in vacuo. The yield was 88%. Mp 25°-26° C.

EXAMPLE 4

2-(BENZOYLOXY)-(N-METHYL-N-ETHOXYCARBONYLMETHYL)ACETAMIDE

A solution of (benzoyloxy)acetyl chloride (0.8 g , 4 mmole) in 4 ml of benzene was added to a cooled (about 5° C.) solution of sarcosine ethyl ester hydrochloride (0.894 g, 12 mmole) in 6 ml of 2M sodium hydroxide. The mixture was stirred vigorously at room temperature for 2 h. The layers were separated and the aqueous phase re-extracted with ethyl acetate (20 ml). The combined organic extracts were washed with 2M hydrochloric acid (10 ml), and dried. Evaporation in vacuo afforded an oily residue which crystallized by trituration with petroleum ether at −20° C.

Recrystallization from ether-petroleum ether yielded the title compound (0.68 g, 61%). Mp 39°-40° C.

EXAMPLE 5

1METHYL-4-(BENZOYLOXYACETYL)PIPERAZINE HYDROCHLORIDE

A solution of 1-methylpiperazine (0.40 g, 4 mmole) in 5 ml benzene was added dropwise while stirring to a solution of (benzoyloxy)acetylchloride (0.80 g, 4 mmole) in 10 ml of benzene. After the addition was completed (about 10 min) the reaction mixture was stirred at room temperature for 1 h. Ether (10 ml) was added and the mixture was filtered. The white crystalline compound on the filter was washed with ether and finally recrystallized from ethanol, yielding 0.70 g (59%) of the title compound. Mp 227°-228° C.

EXAMPLE 6

2-BENZOYLOXY)-(N-METHYL-N-βHYDROXYETHYL)ACETAMIDE

A solution of (benzoyloxy)acetyl chloride (1.5 g, 8 mmole) in 8 ml of benzene was mixed with N-methylethanolamine (1.8 g, 24 mmole). The solution was stirred at room temperature for 3 h and then concentrated in vacuo. The residue was dissolved in ethyl acetate (50 ml) and water (10 ml). The layers were separated and the organic phase washed with 2M hydrochloric acid (5 ml), water (5 ml), dried and evaporated in vacuo. The residue crystallized by trituration with ether and standing overnight at −20° C. The compound was filtered off and recrystallized from ethyl acetate-petroleum ether, giving 1.1 g (50%) of the title compound. Mp 78°-80° C.

EXAMPLE 7

2-(BENZOYLOXY)-N,N-(DICARBAMOYLMETHYL)ACETAMIDE

A solution of (benzoyloxy)acetyl chloride 0.8 g. 4 mmole) in benzene (4 ml) was added while stirring at room temperature to a mixture of iminodiacetamide hydrochloride (1.06 g, 6 mmole) and sodium bicarbonate (2.52 g, 30 mmole) in water (5 ml). The mixture was stirred for 3 h. The precipitate formed was filtered off, washed with a small amount of water and recrystallized from water to give 0.70 g (60%) of the title compound. Mp 195°-196° C.

EXAMPLE 8

N-(BENZOYLOXYMETHYLCARBONYL)PYRROLIDONE

A mixture of (benzoyloxy)acetyl chloride (1.98 g, 0.01 mole), pyrrolidone (0.85 g, 0.01 mole) and pyridine (0.8 g, 0.01 mole) in acetone (10 ml) was refluxed for 3 h. The cooled mixture was filtered and evaporated in vacuo. The residue was dissolved in ethyl acetate (50 ml) and the solution washed with a 2% aqueous solution of sodium bicarbonate, 2M hydrochloric acid and water. After drying over anhydrous sulphate, the organic phase was evaporated under reduced pressure to give a residue which crystallized by addition of ether. Recrystallization from ether-petroleum ether yielded 1.6 g (65%) of the title compound. Mp 83°-84° C.

EXAMPLES 9-33

By following the procedures of the foregoing examples several more esters of benzoic acid according to the invention were prepared. The structure of these esters and their melting points are shown in Table 1.

EXAMPLE 34

2-[1-(P-CHLOROBENZOYL)-5-METHOXY-2-METHYLINDONE-3-ACETYLOXY]-N,N-DIETHYLACETAMIDE

Indomethacin (1.43 g, 4 mmole) and 2-chloro-N,N-diethylacetamide (0.61 g, 4.1 mmole) were dissolved in 5 ml of N,N-dimethylformamide and triethylamine (0.56 ml, 4 mmole) and sodium iodide (60 mg) added. The mixture was stirred at room temperature for 20 h and poured into 50 ml of water. The mixture was extracted with ethyl acetate (2×50 ml). The extract was washed with 2% aqueous solution bicarbonate and water. After drying over anhydrous sodium sulphate the organic phase was evaporated in vacuo. The residue was recrystallized from ethyl acetate-petroleum ether, yielding 1.6 g (90%) of the title compound. Mp 148°–149° C.

TABLE 1

Compounds of Formula I wherein R = phenyl, i.e.

$$\text{Ph-COO(CH}_2)_n\text{-}\underset{\underset{O}{\parallel}}{C}\text{-N}\diagdown_{R_2}^{R_1}$$

| Example number | n | $R_1$ | $R_2$ | Mp (°C.) |
|---|---|---|---|---|
| 9 | 1 | $CH_3$ | $C_2H_5$ | ~20 |
| 10 | 1 | $C_2H_5$ | $C_2H_5$ | 62.5–63.5 |
| 11 | 1 | $C_3H_7$ | $C_3H_7$ | ~20 |
| 12 | 1 | $iC_3H_7$ | $iC_3H_7$ | 104.5–105.5 |
| 13 | 1 | $CH_2CH=CH_2$ | $CH_2CH=CH_2$ | 42–43 |
| 14 | 1 | $nC_4H_9$ | $nC_4H_9$ | ~25 |
| 15 | 1 | $iC_4H_9$ | $iC_4H_9$ | 44–45 |
| 16 | 1 | $CH_3$ | $CH_2CH_2OH$ | 78–80 |
| 17 | 1 | $CH_2CH_2OH$ | $CH_2CH_2OH$ | 80–82 |
| 18 | 1 | $CH_3$ | $CH_2CONH_2$ | 101–102 |
| 19 | 1 | $CH_3$ | $C_6H_{11}$ | 100–101 |
| 20 | 1 | $C_6H_{11}$ | $C_6H_{11}$ | 162–163 |
| 21 | 2 | $CH_3$ | $CH_3$ | <20 |
| 22 | 3 | $CH_3$ | $CH_3$ | 40–41 |
| 23 | 1 | $C_2H_5$ | $CH_2CH_2OH$ | 79–80 |
| 23a | 1 | $CH_3$ | $CH_2CH_2N-$<br>$-(CH_3)_2$, HCl | 158–159 |
| 23b | 1 | $CH_2CH_2OCH_3$ | $CH_2CH_2OCH_3$ | 57–58 |

| Example number | n | $R_1$ | Mp (°C.) |
|---|---|---|---|
| 24 | 1 |  | 74–75 |
| 25 | 1 | 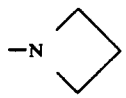 | 57.5–58 |
| 26 | 1 |  | 87–88 |

TABLE 1-continued

Compounds of Formula I wherein R = phenyl, i.e.

$$\text{Ph-COO(CH}_2)_n\text{-}\underset{\underset{O}{\parallel}}{C}\text{-N}\diagdown_{R_2}^{R_1}$$

| Example number | n | $R_1$ | Mp (°C.) |
|---|---|---|---|
| 27 | 1 | 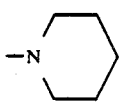 | 107–108 |
| 28 | 1 | 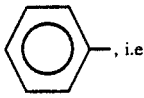 | 103–104 |
| 29 | 1 |  | 118–118.5 |
| 30 | 1 | 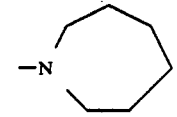 | 194–195 |
| 31 | 1 | 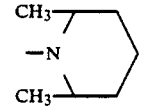 | 72–73 |
| 32 | 1 |  | 121–122 |
| 33 | 1 |  | 228–229 |
| 33a | 1 | 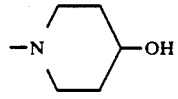 | 54–55 |

EXAMPLE 35

2-[(+)-6-METHOXY-α-METHYL-2-NAPHTHALENEACETYLOXY]-N,N-DIETHYLACETAMIDE

Naproxen (1.07 g, 5 mmole) and 2-chloro-N,N-diethyl-acetamide (0.90 g, 6 mmole) were dissolved in 7 ml of N,N-dimethylformamide and triethylamine (1.4 ml, 10 mmole) and sodium iodide (76 mg) were added. The mixture was refluxed for 2 h, cooled and poured into 35 ml of water. The precipitate formed after standing overnight at 4° C. was collected by filtration, washed with water and recrystalized from 95% ethanol, yielding 1.5 g (92%) of the title compound. Mp 89°–89.5° C.

EXAMPLE 36

2-[2-(ACETYLOXY)BENZOYLOXY]-N,N-DIETHYLACETAMIDE

To a mixture of acetylsalicylic acid (5.4 g. 0.03 mole) and 2-chloro-N,N-diethylacetamide (4.5 g, 0.03 mole) in 40 ml of ethyl acetate was added triethylamine (4.2 ml, 0.03 mole) and sodium iodide (0.45 g, 0.003 mole). The mixture was refluxed for 4 h. After cooling the mixture was filtered and the filtrate washed with 2M hydrochloric acid, 5% sodium bicarbonate and water. After drying over anhydrous sodium sulphate the solution was evaporated in vacuo leaving an oil which crystallized by trituration with ethanol. Recrystallization from 80% ethanol afforded 6.2 g (70%) of the title compound. Mp 75°–76° C.

EXAMPLE 37

2-[2-HYDROXYBENZOYLOXY]-(N-METHYL-N-CARBAMOYLMETHYL)-ACETAMIDE

The ester was prepared from salicylic acid and N-chloroacetylsarcosinamide (prepared as described in Example 87) by the procedure described in Example 1. The crude product was recrystallized from ethyl acetate-ether. Mp 142°–143° C.

EXAMPLE 38

2-(L-PHENYLALANYLOXY)-N,N-DIETHYLACETAMIDE HYDROBROMIDE

A solution of N-benzyloxycarbonyl-L-phenylalanine (3.0 g, 0.01 mole). 2-chloro-N,N-diethylacetamide (1.57 g, 0.011 mole) and triethylamine (1.4 ml, 0.01 mole) in acetonitrile (15 ml) was refluxed for 6 h. evaporated to dryness in vacuo, and diluted with saturated aqueous sodium bicarbonate solution. N-Benzyloxycarbonyl-L-phenylalanine N-N-diethylglycolamide ester was collected by filtration, washed with water and recrystallized from ethanol-water. Mp 85.5°–86.5° C.

This compound (2.0 g) was treated with 10 ml of 33% hydrogen bromide in acetic acid for 1 h at room temperature. Addition of ether precipitated the title compound, which was washed with ether and recrystallized from methanol-ether. Mp 95°–97° C.

EXAMPLE 39

2-[1-(P-CHLOROBENZOYL)-5-METHOXY-2-METHYLINDOLE-3-ACETYLOXY]-N,N-DIMETHYLACETAMIDE a. To a stirred suspension of indomethacin (3.58 g, 0.01 mole) in benzene (10 ml) at 60° C. was added dropwise thionyl chloride (1.12 ml, 0.015 mole). The mixture was stirred for 1 h at 65°–70° C. and concentrated to about 5 ml in vacuo. Hot petroleum ether (25 ml) was added and the mixture filtered to give 3.2 g (85%) of 1-(p-chlorobenzoyl)-5-methoxy-2-methylindole-3-acetyl chloride (acid chloride of indomethacin). Mp 126°–127° C.

b. 2-Hydroxy-N,N-dimethylacetamide was prepared by alkaline hydrolysis of 2-(benzoyloxy)-N,N-dimethylacetamide obtained as described in Example 1. 2-(Benzoyloxy)-N,N-dimethylacetamide (20.7 g, 0.1 mole) was dissolved in 50 ml of ethanol by heating to 40°–50° C. Potassium hydroxide (2M, 70 ml) was added and the mixture allowed to stand at room temperature for 1 h. The pH of the solution was adjusted to 8.9 by addition of 4M hydrochloric acid and the ethanol removed in vacuo. The pH of the mixture was adjusted to 3.5–4 with hydrochloric acid. Precipitated benzoic acid was filtered off and the filtrate was made alkaline (pH 8–9) with potassium hydroxide. The solution was evaporated in vacuo. The semisolid residue obtained was slurried in ethyl acetate (100 ml) and the mixture heated to about 60° C. It was filtered, dried over sodium sulphate and evaporated in vacuo to give crude 2-hydroxy-N,N-dimethylacetamide. This extraction process was repeated twice. Recrystallization from ether-petroleum ether afforded 7.1 g (69%) of the compound. Mp 49°–50° C.

c. Indomethacin acid chloride (1.14 g, 3 mmole) was added in portions to a solution of 2-hydroxy-N,N-dimethylacetamide (340 mg, 3.3 mmole) in acetonitrile (3 ml) and pyridine (320 g, 4 mmole). cooled to 0°–4° C. The mixture was stirred at room temperature for 4 h and evaporated in vacuo. The residue was taken up in a mixture of water and ethyl acetate. The organic base was separated and washed with 1M hydrochloric acid, 5% sodium bicarbonate and water. Evaporation of the dried solution afforded a solid residue which upon recrystallization from ethyl acetate afforded the title compound. Mp 149°–150° C.

EXAMPLE 40

2-(4-AMINOBENZOYLOXY)-N,N-DIETHYLACETAMIDE

A mixture of 4-aminobenzoic acid (1.37 g. 0.01 mole), 2-chloro-N,N-diethylacetamide 2.0 ml, 0.015 mole) and 1.8-diazabicyclo[5.4.0]-undec-7-ene (1.52 g, 0.01 mole) in benzene (20 ml) was stirred at 80° C. for 4 h and then evaporated in vacuo. The residue was taken up in ethyl acetate. After washing with 5% sodium bicarbonate and water the ethyl acetate extract was dried and evaporated in vacuo leaving crude title compound. Recrystallization from ethanol-water gave 1.5 g (60%). Mp 135°–136° C.

EXAMPLE 41

2-[α-METHYL-4-(2-METHYLPROPYL)BENZENEACETYLOXY]-(N-METHYL-N-CARBAMOYLMETHYL)ACETAMIDE

A mixture of ibuprofen (1.03 g, 5 mmole), 2-chloroacetylsarcosinamide (0.82 g, 5 mmole), triethylamine (0.8 ml, 5.7 mmole) and sodium iodide (100 mg) in N,N-dimethylformamide (10 ml) was stirred at room temperature for 20 h. Water (50 ml) was added and the mixture allowed to stand at 4° C. for 5 h. The title compound precipitated was isolated by filtration, washed with water and recrystallized from ethanol-water to give 1.35 g (81%). Mp 100°–100.5° C.

EXAMPLE 42

2-[2-[(2,3-DIMETHYLPHENYL)AMINO]-BENZOYLOXY]-N,N-DIMETHYLACETAMIDE

A mixture of mefenamic acid (2.41 g, 0.01 mole), 2-chloro-N,N-dimethylacetamide (1.6 g, 0.013 mole), triethylamine (1.6 ml, 0.011 mole) and sodium iodide (0.15 g, 0.001 mole) in N,N-dimethylformamide (10 ml) was stirred at 90° C. for 2 h. Water (50 ml) was added and the mixture allowed to stand at 4° C. for 5 h. The title compound was isolated by filtration, washed with water and recrystallized from ethanol-water (3.0 g, 92%). Mp 85°-86° C.

EXAMPLE 43

2-[1-METHYL-5-(α-METHYLBENZOYL)-2H-PYRROLE-2-ACETYLOXY]-N,N-DIMETHYLACETAMIDE

A mixture of tolmetin (1.29 g, 5 mmole), 2-chloro-N,N-dimethylacetamide (0.74 g, 6 mmole), triethylamine (0.84 ml, 6 mmole) and sodium iodide (50 mg) in N,N-dimethylformamide (10 ml) was stirred at 90° C. for 3 h. Water (50 ml) was added and the mixture extracted with ethyl acetate (75 ml). After washing with an aqueous bicarbonate solution and water the extract was dried and evaporated in vacuo. The residue obtained crystallized upon standing at −20° C. and was recrystallized from ethanol-ether to give 1.3 g (76%) of the title compound. Mp 108°-109° C.

EXAMPLE 44

2-[(+)-6-METHOXY-α-METHYL-2-NAPHTHALENEACETYLOXY]-N,N-(DI-β-HYDROXYETHYL)ACETAMIDE

The compound was prepared from naproxen and 2-chloro-N,N-(di-β-hydroxyethyl)acetamide by the procedure described in Example 1. The yield was 60%. Recrystallization from ethyl acetate gave an analytically pure product. Mp 113°-114° C.

EXAMPLE 45

2-[(+)-6-METHOXY-60-METHYL-2-NAPHTHALENEACETYLOXY]-(N-METHYL-N-βHYDROXYETHYL)ACETAMIDE

The compound was prepared from naproxen and 2-chloro (N-methyl-N-βhydroxyethyl)acetamide by the procedure described in Example 1. The yield was 65%. Recrystallization from ethyl acetate gave an analytically pure product. Mp 109°-111° C.

EXAMPLE 46

2-(6-PHENYLACETAMIDOPENICILLANOYLOXY)-N,N-DIETHYL-ACETAMIDE

A mixture of benzylpenicillin sodium (1.78 g, 5 mmole), 2-chloro-N,N-diethylacetamide (1.05 g, 7 mmole) and sodium iodide (75 mg) in N-N-dimethylformamide (10 ml) was stirred at room temperature for 18 h. Water (60 ml) was added and mixture extracted with ethyl acetate (2×50 ml). The extract was washed with 5% aqueous sodium bicarbonate and water. Evaporation of the dried organic phase in vacuo yielded a residue which crystallized from ethanol-water. Mp 60°-61° C.

EXAMPLE 47

2-(BENZOYLOXY)-(N-METHYL-N-(N,N-DIMETHYLGLYCYLOXYETHYL)ACETAMIDE (MONOFUMARATE)

A mixture of 2-(benzoyloxy)-(N-methyl-N-β-hydroxyethyl)-acetamide (0.95 g, 4 mmole), N,N-dimethylglycine (0.41 g, 4 mmole), N,N'-dicyclohexylcarbodiimide (0.82 g, 4 mmole) and 4-toluenesulfonic acid (50 mg) in pyridine (10 ml) was stirred at room temperature for 24 h Methylene chloride (20 ml) was added. The mixture was filtered and the filtrate was evaporated in vacuo. The residue was extracted with 20 ml of boiling ethyl acetate and the extract was evaporated. The oily residue obtained was dissolved in ether (20 ml) and a solution of fumaric acid in 2-propanol was added. After standing overnight at 4° C. the title compound was isolated by filtration in a yield of 59%. Recrystallization from methanol-ether gave an analytically pure product. Mp 127°-127.5° C.

EXAMPLE 48

2-(L-4-HYDROXYPHENYLALANYLOXY)-N,N-DIETHYLACETAMIDE HYDROCHLORIDE

A mixture of N-tert-butoxycarbonyl L-tyrosine (Boc-L-tyrosine) (1.41 g, 5 mmol), 2-chloro-N,N-diethylacetamide (0.68 ml, 5 mmol), tri-ethylamine (0.7 ml, 5 mmol) and sodium iodide (75 mg, 0.5 mmol) in N,N-dimethylformamide (5 ml) was stirred overnight at room temperature. Water (50 ml) was added and the mixture extracted with ethyl acetate (2×50 ml). After washing with an aqueous sodium bicarbonate solution and water the combined extracts were dried and evaporated in vacuo. The solid residue was recrystallized from ethyl acetate to give 1.3 g of Boc-L-tyrosine ester of 2-hydroxy-N,N-diethylacetamide, Mp 130°-131° C.

This ester was deprotected by stirring 0.5 g in 3 ml of 2.5M methanolic HCl. After 1 h a clear solution was obtained. The solution was evaporated in vacuo and the oily residue crystallized from ethanol-ether. Mp 164°-166° C.

EXAMPLE 49

2-(4-HYDROXYBENZOYLOXY)-N,N-DIETHYLACETAMIDE

A mixture of 4-hydroxybenzoic acid (1.38 g, 0.01 mol), 2-chloro-N,N-diethylacetamide (1.4 g, 0.01 mol) triethylamine (1.44 ml. 0.01 mol) and sodium iodide (150 mg, 0.001 mol) in N,N-dimethylformamide (6 ml) was stirred at room temperature for 18 h. Water (100 ml) was added and the mixture allowed to stand at 4° C. for 5 h. The title compound was isolated by filtration, washed with water and recrystallized from ethanol-water to give 1.8 g. Mp 148°-149° C.

EXAMPLE 50

2-TRANS-4-(AMINOMETHYL)CYCLOHEXANOYLOXY)-N,N-DIMETHYLACETAMIDE HYDROCHLORIDE

Tranexamic acid (3.0 g, 0.019 mol) was dissolved in 12 ml of thionyl chloride. The solution was kept at room temperature for 30 min. Upon addition of ether the acid chloride of tranexamic acid as hydrochloride salt precipitated. It was filtered off and dried over $P_2O_5$ in vacuo, mp 138°-139° C.

The acid chloride (2.10 g, 0.01 mol) was added portionwise and while stirring to a solution of 2-hydroxy-N,N-dimethylacetamide (1.24 g, 0.012 mol) in 10 ml of dioxane. The solution was stirred at 60° C. for 1 h and then cooled to 0°-4° C. The precipitate formed was filtered off and recrystallized from ethanol to give 1.5 g of the title compound, mp 183°-184° C.

EXAMPLE 51

2-[α-METHYL-4-(2-METHYLPROPYL)BENZENEACETYLOXY]-(N-METHYL-N-(N'-MORPHOLINOMETHYLCARBAMOYL)METHYL)ACETAMIDE HYDROCHLORIDE

2-[α-Methyl-4-(2-methylpropyl)benzeneacetyloxy]-(N-methyl-N-carbamoylmethyl)acetamide (0.67 g, 2 mmol), prepared as described in Example 49, was dissolved in 2.5 ml of methanol. Morpholine (0.18 g. 2 mmol) and 0.17 ml of 37% aqueous formaldehyde solution were added The solution was heated on a steam bath for 15 min. and evaporated in vacuo. The oily residue was dissolved in ether (10 ml) and a 2.5M methanolic solution of HCl (1 ml) was added followed by petroleum ether. The mixture was kept overnight at $-20°$ C. to allow precipitation of the title compound which was isolated by filtration, mp 154°-155° C.

EXAMPLES 52-86

By following the procedures of the foregoing examples several more novel esters of the present invention were prepared. The structure of these esters along with their melting points are shown in Table 2.

TABLE 2

Compounds of Formula I wherein n = 1

| Example number | R—COO— is the acyloxy residue of: | $R_1$ | $R_2$ | Mp (°C.) |
|---|---|---|---|---|
| 52 | Naproxen | $CH_3$ | $CH_3$ | 150-151 |
| 53 | Naproxen | $CH_3$ | $CH_2CONH_2$ | 179-180 |
| 54 | Ibuprofen | $CH_3$ | $CH_3$ | oil |
| 55 | Ketoprofen | $CH_3$ | $CH_3$ | oil |
| 56 | Ketoprofen | $C_2H_5$ | $C_2H_5$ | oil |
| 57 | 4-Biphenylacetic acid | $CH_3$ | $CH_2CONH_2$ | 174-175 |
| 58 | Flurbiprofen | $CH_3$ | $CH_3$ | 74-75 |
| 59 | Flurbiprofen | $C_2H_5$ | $C_2H_5$ | 60-61 |
| 60 | Fenbufen | $CH_3$ | $CH_3$ | 120-121 |
| 61 | Fenbufen | $C_2H_5$ | $C_2H_5$ | 94-95 |
| 62 | Indomethacin | $C_2H_5$ | $C_2H_5$ | 104-105 |
| 63 | Indomethacin | $CH_3$ | $CH_2CH_2OH$ | 138-139 |
| 64 | Indomethacin | $CH_2CH_2OH$ | $CH_2CH_2OH$ | 144-146 |
| 65 | Tolfenamic acid | $CH_3$ | $CH_3$ | 106-107 |
| 66 | Tolfenamic acid | $C_2H_5$ | $C_2H_5$ | 114-115 |
| 67 | Tolfenamic acid | $C_2H_5$ | $CH_2CH_2OH$ | 85-86 |
| 68 | Tolfenamic acid | $CH_2CH_2OH$ | $CH_2CH_2OH$ | 176-180 |
| 69 | Diflunisal | $CH_3$ | $CH_3$ | 96.5-97 |
| 70 | Diflunisal | $C_2H_5$ | $C_2H_5$ | 75-76 |
| 71 | Mephenamic acid | $CH_3$ | $CH_2CH_2OH$ | 176-180 |
| 72 | L-methyldopa | $C_2H_5$ | $C_2H_5$ | 122-124 |
| 73 | Sulindac | $C_2H_5$ | $C_2H_5$ | 100-101 |
| 74 | Benzylpenicillin | $CH_3$ | $CH_3$ | 71-72 |
| 75 | Furosemide | $CH_3$ | $CH_3$ | 193-194 |
| 76 | Mecillinam | $C_2H_5$ | $C_2H_5$ | 120-122 |
| 77 | Valproic acid | $CH_3$ | $CH_3$ | oil |
| 78 | Valproic acid | $CH_3$ | $CH_2CONH_2$ | 57-58 |
| 79 | Salicylic acid | $CH_3$ | $CH_3$ | 67.5-68 |
| 80 | Salicylic acid | $C_2H_5$ | $C_2H_5$ | 73-74.5 |
| 81 | Acetylsalicylic acid | $C_3H_7$ | $C_3H_7$ | 49.5-50.5 |
| 82 | Acetylsalicylic acid | $iC_3H_7$ | $iC_3H_7$ | 108-109 |
| 83 | Acetylsalicylic acid | $CH_3$ | $CH_2COOC_2H_5$ | 47-48 |
| 84 | Acetylsalicylic acid | $CH_3$ | $CH_2CONH_2$ | 123-124 |
| 85 | Acetylsalicylic acid | $C_6H_{11}$ | $C_6H_{11}$ | 133-134 |
| 86 | Acetylsalicylic acid | | morpholine | 97-99 |

EXAMPLE 87

PREPARATION OF α-CHLOROACETYLSARCOSINAMIDE

Sarcosinamide hydrochloride was prepared by reacting methylamine with 2-chloroacetamide as described by Marvel et al. (1946). The compound was recrystallized from ethanol. Mp 160°-161° C.

A solution of chloroacetyl chloride (0.1 mole, 11.3 g) in benzene (40 ml) was added over 30 min to a mixture of sarcosinamide hydrochloride (0.1 mole, 12.45 g) and sodium bicarbonate (0.25 mole, 20.0 g) in 40 ml of water. The mixture was vigorously stirred for 3 h at room temperature. The aqueous phase was acidified with 5M hydrochloric acid to pH 5 and extracted with ethyl acetate (3×400 ml). The combined extracts were dried over anhydrous sodium sulphate and evaporated in vacuo. The solid residue obtained was recrystallized from ethanol-ether to give 8.5 g (52%) of the title compound. Mp 85°-86° C.

EXAMPLE 88

2-(ACETYLOXY)-N,N-DIMETHYLACETAMIDE

A suspension of anhydrous sodium acetate (16.4 g, 0.2 mole) and 2-chloro-N,N-dimethylacetamide (24.3 g, 0.2 mole) in toluene (70 ml) was refluxed for 4 h. After cooling to room temperature the mixture was filtered and the filtrate washed with water (2×10 ml), dried and evaporated in vacuo. The solid residue obtained was recrystallized from ether yielding 22.0 g (76%). Mp 52°-53° C.

IN-VITRO CLEAVAGE OF ESTER PRODRUGS

Reaction conditions

Solutions of various derivatives of this invention in aqueous buffer solutions or 50-80% human plasma solutions (pH 7.4) were kept at 37° C. The initial concentration of the derivatives was in the range $3\times10^{-4}$-$10^{-5}$M. At various times an aliquot of the solutions was withdrawn and analyzed by HPLC for remaining derivative as well as for parent acid. For the plasma solutions the aliquot withdrawn was deproteinized with methanol, ethanol or acetonitrile and after centrifugation, the clear supernatant was injected on HPLC.

Analytical method

An HPLC method was used for the determination of the ester derivatives and their parent acids. In this method a reversed-phase LiChrosorb RP-8 column (250×4 mm) was eluted at ambient temperature with mixtures of methanol and 0.01M acetate buffer pH 5.0, methanol and 0.01M phosphate buffer pH 4.5 or methanol and 0.02M phosphate buffer pH 3.5. the composition of the eluant was adjusted for each compound in order to provide an appropriate retention time and separation of ester and the corresponding acid. The flow-rate was 0.6-1.6 ml/min and the column effluent was monitored spectrophotometrically at an appropriate wavelength. Quantitation of the compounds was done by measurement of the peak heights in relation to those of standards chromatographed under the same conditions.

The various prodrug esters were found to be cleaved quantitatively to the parent acids in human plasma solutions. An example is shown in FIG. 1. The esters of the present invention hydrolyzed surprisingly rapidly in human plasma although the rate of hydrolysis depends greatly on the substituents $R_1$ and $R_2$ in Formula I. The half-lives of hydrolysis of various derivatives in 50% human plasma solutions (pH 7.4; 37° C.) are given in Table 3. As can be seen from the data the N,N-disubstituted 2-(acyloxy)acetamide esters are particularly rapidly hydrolyzed. Thus, the half-life for the hydrolysis of 2-(benzoyloxy)-N,N-diethylacetamide is less than 3 sec. In pure buffer solution of the same pH (7.4) and at 37° C. the half-life of hydrolysis of this compound and the related esters listed in Table 3 was found to be greater than 1,000 h, thus demonstrating the facile enzymatic hydrolysis at conditions similar to those prevailing in vivo.

Figure 2:
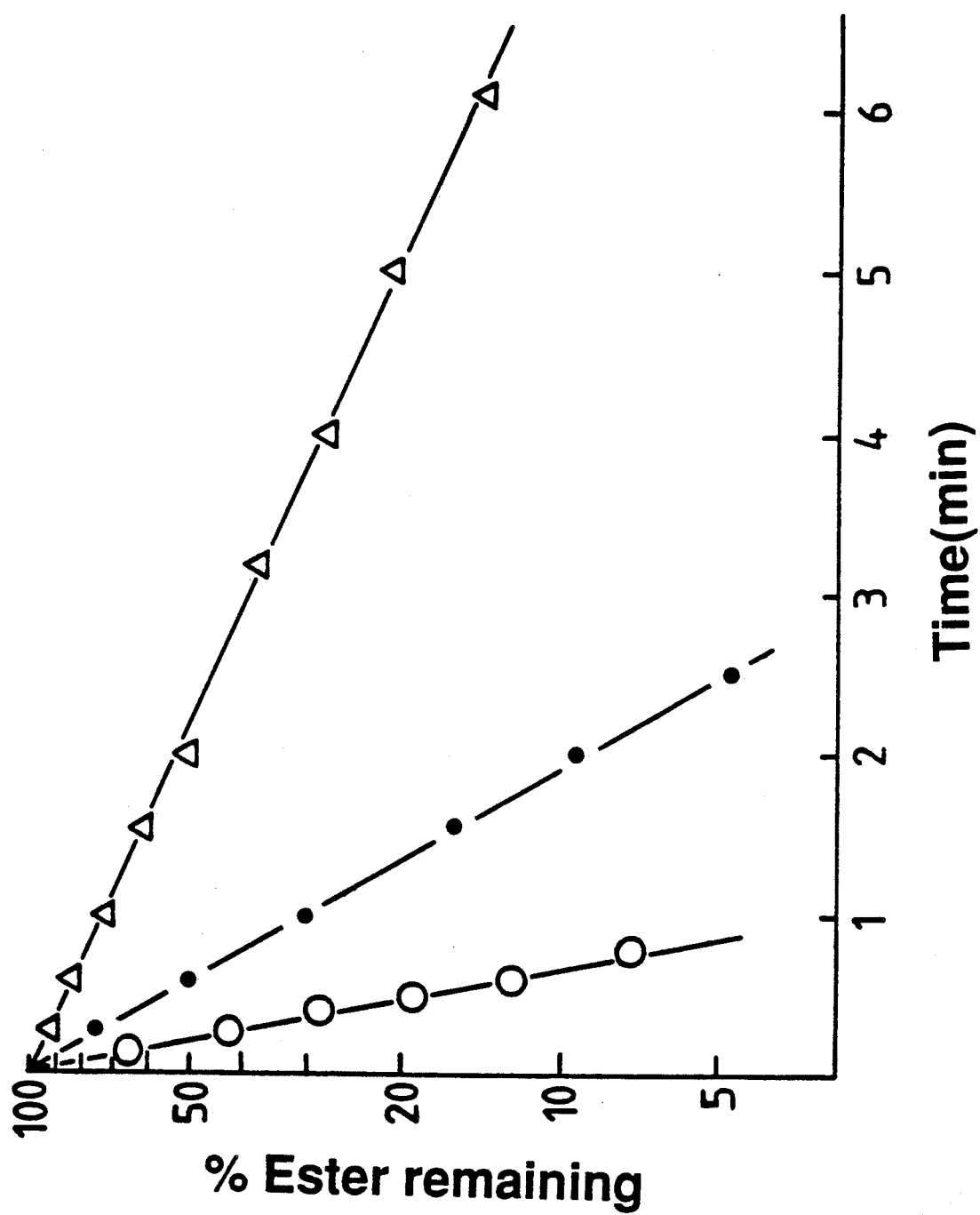
FIG. 2 shows plots of the first-order kinetics of hydrolysis of various esters (initial concentration being $10^{-4}$M) in 80% human plasma at 37° C. Key: o, N,N-diethylglycolamide ester of L-phenylalanine; ●, N,N-diethylglycolamide ester of naproxen; △, N-methyl, N-carbamoylmethylglycolamide ester of ketoprofen.
Figure 3:
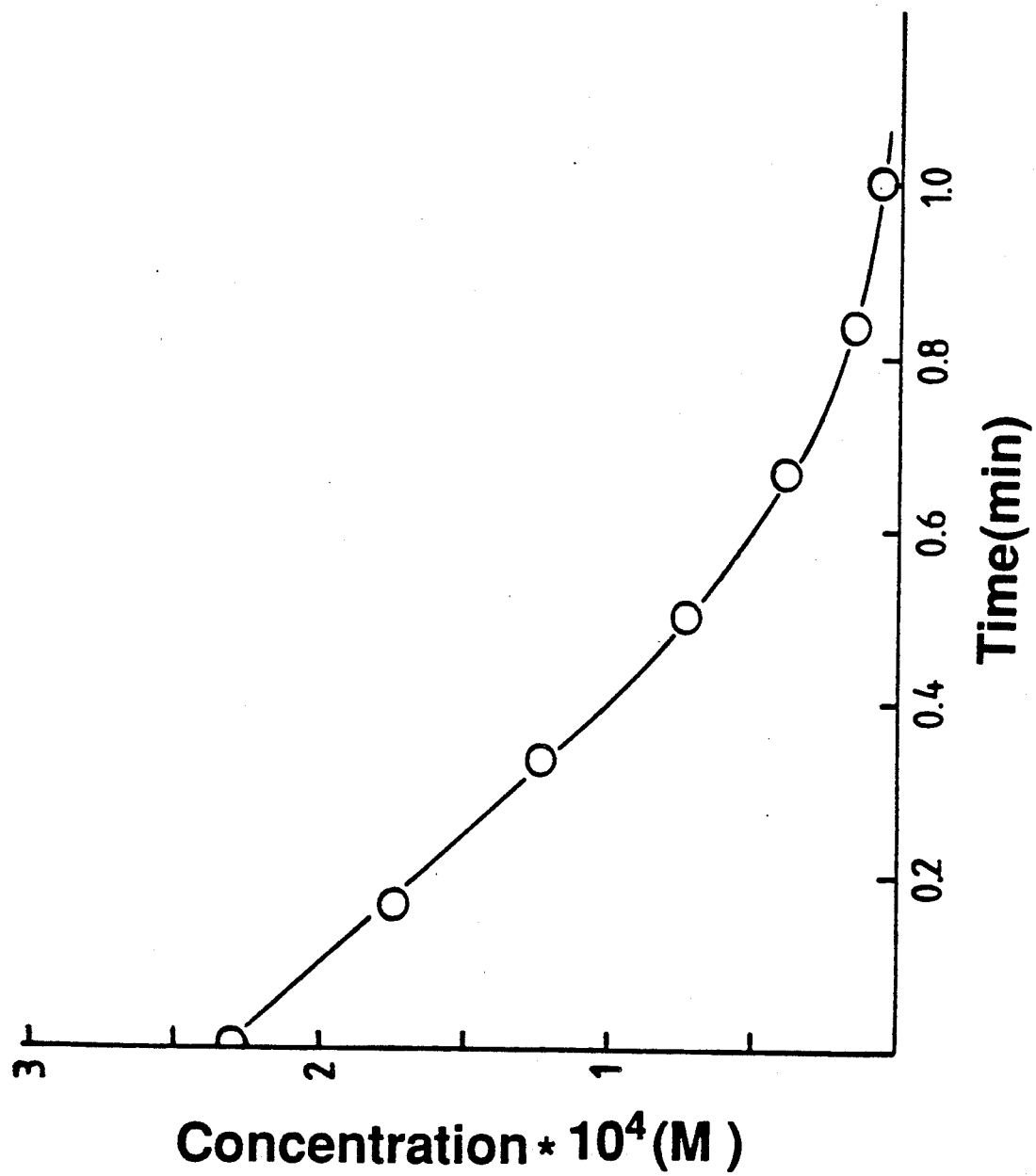
FIG. 3 shows plot of the rate of hydrolysis of the N,N-dimethylglycolamide ester of salicylic acid in 80% human plasma at 37° C.

At initial concentrations of about $10^{-4}$M the progress of hydrolysis of some esters followed strict first-order kinetics (examples are shown in FIG. 2), whereas in other cases mixed kinetics was observed. An example of the latter is shown in FIG. 3. As seen from FIG. 3 the rate of hydrolysis initially followed zero-order kinetics and as the substrate depleted, it changed to follow first-order kinetics. This behaviour is typical for enzyme-catalyzed reactions in which the initial substrate concentration is higher than the Michaelis constant $K_m$. At low substrate concentrations, i.e. concentrations similar to those prevailing in vivo for prodrug hydrolysis, the enzymatic reaction is first-order with the half-lives referred to in Table 3.

Table 4 shows hydrolysis data for esters of various carboxylic acids according to the present invention. The structure of the acyl moiety has an influence on the enzymatic reactivity but in all cases a quite rapid rate of hydrolysis in plasma was observed. By comparing the rates of hydrolysis of the esters of the present invention with those of the corresponding simple methyl or ethyl esters (Table 5) the much more facile enzymatic hydrolysis of the esters disclosed herein is readily apparent.

The esters of the present invention were found to be highly stable in acidic media. For example, no hydrolysis, i.e. (<1%), of 2-(benzoyloxy)-N,N-diethylacetamide was found to take place in 0.01M HCl solutions kept at 37° C. for 3 h.

These results show that the esters of the present invention combine a high susceptibility to undergo enzymatic hydrolysis in plasma with a high stability in aqueous solution, e.g. in acidic medium such as gastric juices. In consequence, for example, the esters will remain intact in the gastro-intestinal tract upon oral administration, the release of the free carboxylic acid agent occurring during the absorption process or in the blood following absorption.

WATER-SOLUBILITY AND LIPOPHILICITY OF THE ESTER PRODRUGS

The partition coefficients (P) for some esters of the present invention were measured at 22° C. using the widely-used octanol-water system. Similarly, the solubility of the derivatives in water or aqueous buffer solutions was determined. The values found for log P and the water-solubilities are included in Table 3.

The results obtained show that by varying the substituents $R_1$ and $R_2$ and n in Formula I it is readily feasible to obtain ester prodrug derivatives with varying and any desirable lipophilicity or water-solubility with retainment of a great lability to enzymatic hydrolysis. Thus, as seen from Table 3, the derivative 2-(benzoyloxy)-N-N-(di-$\beta$-hydroxyethyl)acetamide is soluble in water to an extent of more than 70% w/v although it is a neutral compound with a positive log P value. As a further example, the corresponding ester derivative of naproxen (Example 44) was found to be more than 20-fold more soluble in 0.01M HCl than parent naproxen.

BIOAVAILABILITY STUDY

The naproxen prodrug derivative described in Example 44 was administered orally to rabbits. Similarly, naproxen itself was given orally to rabbits in an equivalent dose (4.8 mg/kg naproxen). After drug adminstration, blood samples were taken at various times and the plasma fraction assayed for naproxen and prodrug using an HPLC method at the following conditions: Column: LiChrosorb RP-8; eluent: methanol-0.02M $KH_2PO_4$ (pH 3.5) 65:35; detection: UV at 230 nm.

As seen from Table 6 the naproxen prodrug derivative is efficiently absorbed following oral administration. No measurable concentrations (<0.1 μg/ml) of intact naproxen prodrug were observed, thus demonstrating that the prodrug is rapidly converted back to naproxen in vivo in accordance with the "prodrug" definition provided at the outset of this application.

TABLE 3

Rates of enzymatic hydrolysis, water-solubility and partition coefficients for various compounds of the formula

| $R_1$ | $R_2$ | n | $S^a$ (mg/ml) | log $P^b$ | $t_{\frac{1}{2}}^c$ (min) |
|---|---|---|---|---|---|
| $CH_3$ | $CH_3$ | 1 | 8.8 | 1.07 | 0.15 |
| $CH_3$ | $C_2H_5$ | 1 | — | 1.27 | 0.10 |
| $C_2H_5$ | $C_2H_5$ | 1 | 2.0 | 2.06 | 0.04 |
| $nC_3H_7$ | $nC_3H_7$ | 1 | 1.1 | 2.65 | 0.14 |
| $iC_3H_7$ | $iC_3H_7$ | 1 | 0.12 | 2.56 | 0.08 |
| $CH_2CH=CH_2$ | $CH_2CH=CH_2$ | 1 | 0.71 | 2.34 | 0.08 |
| $nC_4H_9$ | $nC_4H_9$ | 1 | 0.080 | 3.91 | 3.1 |
| $iC_4H_9$ | $iC_4H_9$ | 1 | 0.081 | 3.80 | <1.5 |
| $CH_3$ | $C_6H_{11}$ | 1 | 0.14 | 2.99 | 0.54 |
| $C_6H_{11}$ | $C_6H_{11}$ | 1 | 0.0034 | — | 407 |
| $CH_3$ | $CH_2CH_2OH$ | 1 | 19.3 | 0.58 | 0.20 |
| $C_2H_5$ | $CH_2CH_2OH$ | 1 | 10.8 | 0.93 | 0.16 |
| $CH_2CH_2OH$ | $CH_2CH_2OH$ | 1 | 720 | 0.17 | 0.42 |
| $CH_3$ | $CH_2CH_2OOC-$ $-CH_2N(CH_3)_2^d$ | 1 | >200 | — | 0.08 |
| $CH_3$ | $CH_2CONH_2$ | 1 | 30.2 | 0.08 | 0.13 |

TABLE 3-continued

Rates of enzymatic hydrolysis, water-solubility and partition coefficients for various compounds of the formula $$\text{Ph-COO(CH}_2)_n\text{-C(=O)-N(R}_1)\text{(R}_2)$$

| $R_1$ | $R_2$ | n | $S^a$ (mg/ml) | log $P^b$ | $t_{1/2}^c$ (min) |
|---|---|---|---|---|---|
| $CH_3$ | $CH_2COOC_2H_5$ | 1 | 6.0 | 1.56 | 0.22 |
| $CH_3$ | $CH_3$ | 2 | 17.6 | 1.28 | 5.6 |
| $CH_3$ | $CH_3$ | 3 | 13.9 | 1.86 | 14.1 |
| $CH_3$ | $CH_2CH_2N(CH_3)_2^d$ | 1 | >100 | — | 0.12 |
| $CH_2CH_2OCH_3$ | $CH_2CH_2OCH_3$ | 1 | — | — | 0.25 |

| $-N(R_1)(R_2)$ | n | $S^a$ (mg/ml) | log $P^b$ | $t_{1/2}^c$ (min) |
|---|---|---|---|---|
| -N(azetidinyl) | 1 | 5.4 | 1.20 | 0.83 |
| -N(pyrrolidinyl) | 1 | 6.3 | 1.44 | 5.7 |
| -N(piperidinyl) | 1 | 0.78 | 1.95 | 2.5 |
| -N(hexamethyleneimino) | 1 | 0.75 | 2.30 | 1.0 |
| -N(morpholino) | 1 | 4.2 | 0.90 | 4.9 |
| -N(4-hydroxypiperidinyl) | 1 | — | — | 5.8 |
| -N(2-methylpiperidinyl) | 1 | 0.15 | 2.90 | 0.40 |
| -N(2-carbamoylpyrrolidinyl) | 1 | 1.5 | 0.20 | 2.3 |
| -N(2-methoxycarbonylpyrrolidinyl) | 1 | 2.4 | 1.42 | 1.9 |
| -N(2-oxopyrrolidinyl) | 1 | 0.49 | 1.83 | 18 |
| -N(4-methylpiperazinyl)$^d$ | 1 | >100 | — | 12.7 |

$^a$Solubility in water at 22° C.
$^b$P is the partition coefficient between octanol and water at 22° C.
$^c$Half-life of hydrolysis in 50% human plasma (pH 7.4) at 37° C.
$^d$Hydrochloride salt

TABLE 4

Half-lives ($t_{1/2}$) of hydrolysis of various compounds of the formula $$\text{R-COO-CH}_2\text{-C(=O)-N(R}_1)\text{(R}_2)$$

in 80% human plasma (pH 7.4) at 37° C.

| R—COO— is the acyloxy residue of | $R_1$ | $R_2$ | $t_{1/2}$ (min) |
|---|---|---|---|
| Naproxen | $CH_3$ | $CH_3$ | 1.5 |
| | $C_2H_5$ | $C_2H_5$ | 0.6 |
| | $CH_2CH_2OH$ | $CH_2CH_2OH$ | 1.3 |
| | $CH_3$ | $CH_2CONH_2$ | 2.5 |
| Ibuprofen | $CH_3$ | $CH_3$ | 8.6 |
| | $CH_3$ | $CH_2CONH_2$ | 9.6 |
| | $CH_3$ | $CH_2CONHCH_2N(morpholino)$ | 10.8 |
| Ketoprofen | $CH_3$ | $CH_3$ | 1.1 |
| | $C_2H_5$ | $C_2H_5$ | 0.5 |
| | $CH_3$ | $CH_2CONH_2$ | 2.3 |

TABLE 4-continued

Half-lives ($t_{\frac{1}{2}}$) of hydrolysis of various compounds of the formula $$R-COO-CH_2-\overset{O}{\underset{\|}{C}}-N\diagup_{R_2}^{R_1} \text{ in 80\% human plasma (pH 7.4) at 37° C.}$$

| R—COO— is the acyloxy residue of | $R_1$ | $R_2$ | $t_{\frac{1}{2}}$ (min) |
|---|---|---|---|
| Flurbiprofen | $CH_3$ | $CH_3$ | 10.8 |
|  | $C_2H_5$ | $C_2H_5$ | 4.7 |
| Fenbufen | $CH_3$ | $CH_3$ | 9.2 |
|  | $C_2H_5$ | $C_2H_5$ | 3.8 |
| Indomethacin | $CH_3$ | $CH_3$ | 130 |
|  | $C_2H_5$ | $C_2H_5$ | 25 |
|  | $CH_3$ | $CH_2CH_2OH$ | 140 |
|  | $CH_2CH_2OH$ | $CH_2CH_2OH$ | 88 |
| Sulindac | $C_2H_5$ | $C_2H_5$ | 26 |
| Tolmetin | $CH_3$ | $CH_3$ | 14.6 |
|  | $C_2H_5$ | $C_2H_5$ | 13.4 |
| Tolfenamic acid | $CH_3$ | $CH_3$ | 2.8 |
|  | $C_2H_5$ | $C_2H_5$ | 5.0 |
|  | $C_2H_5$ | $CH_2CH_2OH$ | 3.0 |
| 4-Aminobenzoic acid | $C_2H_5$ | $C_2H_5$ | 0.6 |
| Tranexamic acid | $CH_3$ | $CH_3$ | 1.2 |
| L-Phenylalanine | $C_2H_5$ | $C_2H_5$ | 0.2 |
| L-Tyrosine | $C_2H_5$ | $C_2H_5$ | 0.5 |
| 4-Hydroxybenzoic acid | $C_2H_5$ | $C_2H_5$ | 1.8 |
| Salicylic acid | $CH_3$ | $CH_3$ | 0.08 |
|  | $C_2H_5$ | $C_2H_5$ | 0.08 |
|  | $CH_3$ | $CH_2CONH_2$ | 0.33 |
|  | —N⟨ ⟩N—$CH_3$ (piperazinyl) |  | 22 |
| Mefenamic acid | $CH_3$ | $CH_3$ | 2.4 |
| Diflunisal | $C_2H_5$ | $C_2H_5$ | 79 |
| 4-Biphenylacetic acid | $CH_3$ | $CH_2CONH_2$ | 2.1 |

TABLE 5

Half-lives ($t_{\frac{1}{2}}$) of hydrolysis of esters of various drugs containing a carboxylic acid function in 80% human plasma[a]

| Acid | Methyl ester $t_{\frac{1}{2}}$ | N,N-diethylglycolamide ester $t_{\frac{1}{2}}$ |
|---|---|---|
| Salicylic acid | 17.6 h | 0.08 min |
| Benzoic acid | 2.0 h | 0.04 min |
| Naproxen | 20.1 h[b] | 0.6 min |
| Ketoprofen | >20 h | 0.5 min |
| Fenbufen | 4.7 h | 3.8 min |
| Tolmetin | 19 h | 13.4 min |
| Tolfenamic acid | 100 h | 5.0 min |
| Indomethacin | 150 h | 25 min |
| L-Phenylalanine | 29 min | 0.2 min |
| 4-Hydroxybenzoic acid | >50 h | 1.8 min |
| 4-Aminobenzoic acid | >100 h[b] | 0.6 min |
| Tranexamic acid | >3 h | 1.2 min[c] |
| L-Tyrosine | 59 min[b] | 0.5 min |

[a] At pH 7.4 and 37° C.
[b] Value for ethyl ester
[c] Value for N,N-dimethylglycolamide ester

TABLE 6

Plasma concentrations of naproxen following oral administration of naproxen (4.8 mg/kg) or the equivalent amount of the N,N-(β-hydroxyethyl)glycolamide ester of naproxen to rabbits.

| Time after administration (min) | Naproxen plasma conc. (µg/ml) After naproxen administration | After ester administration |
|---|---|---|
| 10 | 2.8 | 2.7 |
| 25 | 5.1 | 5.7 |
| 50 | 6.4 | 8.3 |
| 75 | 7.1 | 8.2 |
| 100 | 7.4 | 7.7 |
| 125 | 7.1 | 6.7 |
| 200 | 5.4 | 4.0 |
| 300 | 3.6 | 3.6 |
| 400 | 2.7 | 3.3 |
| 450 | 2.4 | 3.2 |

REFERENCES CITED

Boltze, K.-H. & H. Kreisfeld (1977): *Arzneim.-Forsche.* 27, 1,300–1,312.

Todd, P.A. & R.C. Heel (1986): *Drugs* 31, 198–248.

Concilio, C. & A. Bongini (1966): *Ann. Chim.* (Rome) 56, 417–426.

Hankins, E.M. (1965): U.S. Pat. No. 3,173,900.

Speziale, A.J. & P.C. Hamm (1956): *J. Am. Chem. Soc.* 78, 2,556–2,559.

Berkelhammer, G., S. DuBreuil & R.W. Young (1961): *J. Org. Chem.* 26, 2,281–2,288.

Weaver, W.E. & W.M. Whaley (1947): *J. Am. Chem. Soc.* 69, 515–516.

Ronwin, E. (1953): *J. Org. Chem.* 18, 127–132.

Holysz, R.P. & H.E. Stavely (1950): *J. Am. Chem. Soc.* 72, 4,760–4,763.

Ferres, H. (1983): *Drugs of Today* 19, 499–538.

Harrison, I.T., B. Lewis, P. Nelson, W. Rooks, A. Roszkowski, A. Tomolonis & J. Fried (1970): *J. Med. Chem.* 13, 203–205.

Child, R.G., A.C. Osterberg, A.E. Sloboda & A.S. Tomcufcik (1977): *J. Pharm. Sci.*, 66, 466–476.

Tocco, D.J., F.A. de Luna, A.E.W. Duncan, T.C. Vassil & E.H. Ulm (1982): *Drug Metab. Disp.* 10, 15–19.

Larmour, I., B. Jackson, R. Cubela & C.I. Johnston (1985): *Br. J. Clin. Pharmacol.* 19, 701–704.

Rakhit, A. & V. Tipnis (1984): *Clin. Chem* 30, 1,237–1,239.

Tipnis, V. & A. Rakhit (1985): *J. Chromatogr.* 345, 396–401.

Boltze, K.-H., O. Brendler, H. Jacobi, W. Opitz, S. Raddatz, P.-R. Seidel & D. Vollbrecht (1980): *Arzneim.-Forsch.* 30, 1,314–1,325.

"Remington's Pharmaceutical Sciences", Sixteenth Edition (1980), Mack Publishing Company, Easton, U.S.A.

Marvel, C.S., J.R. Elliott, F.E. Boeltner & H. Yaska (1946): *J. Am. Chem. Soc.* 68, 1,681–1,686.

We claim:

1. Compounds of the formula I $$R-COO-(CH_2)_n-\overset{\overset{O}{\|}}{C}-N\overset{R_1}{\underset{R_2}{}}$$    I wherein R—COO— represents the acyloxy residue of a carboxylic acid drug or medicament selected from:
   Indomethacin
   Naproxen
   Ibuprofen
   Flurbiprofen
   5-Aminosalicylic Acid
   L-Dopa
   Furosemide and
   N-Acetylcysteine and $R_1$ and $R_2$ are the same or different and are selected from a group consisting of an alkyl group, an alkenyl group, an aryl group, an aralkyl group, a cycloalkyl group, in which the alkyl, alkenyl, aryl, aralkyl or cycloalkyl group is unsubstituted or substituted with one or more substituents selected from:
   a halogen atom,
   a hydroxy group,
   a straight or branched-chain alkoxy group having the formula $R_3$—O—, wherein $R_3$ represents an alkyl group or an aryl group, which groups may be unsubstituted or substituted with one or more of a halogen atom or a hydroxy group,
   a carbamoyl group having the formula $$-CON\overset{R_5}{\underset{R_4}{}}$$

wherein $R_4$ and $R_5$ are the same or different and are hydrogen, an alkyl group or are selected from a group having the formula —$CH_2NR_7R_6$, wherein $R_6$ and $R_7$ are the same or different and are hydrogen, or an alkyl group,
   an amino group having the formula —$NR_8R_9$, wherein $R_8$ and $R_9$ are the same or different and are hydrogen, or an alkyl group
   an acyloxy group having the formula —$COOR_{10}$, wherein $R_{10}$ is an alkyl, aryl or aralkyl group,
   an oxyacyl group having the formula $R_{11}COO$— wherein $R_{11}$ is hydrogen, an alkyl group, an aryl group, an aralkyl group, a cycloalkyl group, in which the alkyl, aryl, aralkyl or cycloalkyl group is unsubstituted or substituted with one or more of a halogen atom, a hydroxy group, an alkoxy group of the formula $R_3$—O— as defined above, a carbamoyl group of the formula —$CONR_4R_5$ as defined above or an amino group having the formula —$NR_8R_9$ as defined above;

and nontoxic pharmaceutically acceptable acid addition salts thereof.

2. Compounds according to claim 1 wherein $R_1$ is methyl or ethyl, and $KR_2$ is selected from
   —$CH_3$
   —$CH_2CH_3$
   —$CH_2CH_2OH$
   —$CH_2CONH_2$
   —$CH_2CH_2CONH_2$
   —$CH_2CH_2OOCCH_2N(CH_3)_2$
   —$CH_2CH_2OOCCH_2N(C_2H_5)_2$
   —$CH_2CH_2OOCCH_2NH_2$
   —$CH_2CONHCH_2N(CH_3)_2$
   —$CH_2CONHCH_2N(C_2H_5)_2$
   —$CH_2CH_2N(CH_3)_2$
   —$CH_2CONHCH_2NH_2$
   —$CH_2CONH$—$CH_3$.

3. Compounds of the formula I $$R-COO-(CH_2)_n-\overset{\overset{O}{\|}}{C}-N\overset{R_1}{\underset{R_2}{}}$$    I wherein $R_1$ and $R_2$ both are alkyl or both are —$CH_2CH_2OH$ and R—COO is the acyloxy residue of a carboxylic acid drug selected from:
   Indomethacin
   Naproxen
   Ibuprofen
   Flurbiprofen
   5-Aminosalicylic acid
   L-Dopa
   Furosemide and
   N-Acetylcysteine.

4. Compounds according to claim 1, wherein R—COO is derived from Naproxen.

5. Compounds according to claim 3, wherein R—COO is derived from Naproxen.

6. Compounds according to claim 1, wherein R—COO is derived from L-Dopa or N-acetylcysteine.

7. Compounds according to claim 3, wherein R—COO is derived from L-Dopa or N-acetylcysteine.

8. A pharmaceutical composition comprising a pharmaceutically acceptable excipient and a pharmaceutically effective amount of a compound according to any one of claims 1–7.

* * * * *

UNITED STATES PATENT AND TRADEMARK OFFICE
CERTIFICATE OF CORRECTION

PATENT NO. : 5,073,641
DATED : December 17, 1991
INVENTOR(S) : Hans Bundgaard et al It is certified that error appears in the above-identified patent and that said Letters Patent is hereby corrected as shown below:

Column 37, claim 1, in formula I, "$(CH_2)$" should read --$CH_2$--.

Column 38, claim 2, line 2, "$KR_2$" should correctly read --$R_2$--.

Column 38, claim 3, in formula I, "$(CH_2)n$" should correctly read --$CH_2$--.

Signed and Sealed this

First Day of June, 1993

Attest:

MICHAEL K. KIRK

Attesting Officer

Acting Commissioner of Patents and Trademarks